(12) United States Patent
Jangbarwala

(10) Patent No.: US 8,598,240 B2
(45) Date of Patent: Dec. 3, 2013

(54) FISCHER-TROPSCH PROCESS USING FIBROUS COMPOSITE CATALYTIC STRUCTURES HAVING AT LEAST THREE SOLID PHASES

(71) Applicant: Juzer Jangbarwala, Chino Hills, CA (US)

(72) Inventor: Juzer Jangbarwala, Chino Hills, CA (US)

( * ) Notice: Subject to any disclaimer, the term of this patent is extended or adjusted under 35 U.S.C. 154(b) by 0 days.

(21) Appl. No.: 13/680,416

(22) Filed: Nov. 19, 2012

(65) Prior Publication Data

US 2013/0085189 A1 Apr. 4, 2013

Related U.S. Application Data

(63) Continuation-in-part of application No. 11/893,829, filed on Aug. 17, 2007, now Pat. No. 8,314,044.

(51) Int. Cl.
*C07C 27/00* (2006.01)

(52) U.S. Cl.
USPC .......................................... 518/715; 518/700

(58) Field of Classification Search
USPC .................................................. 518/700, 715
See application file for complete search history.

(56) References Cited

U.S. PATENT DOCUMENTS

2004/0097371 A1\* 5/2004 Jangbarwala ................. 502/439
2005/0229489 A1\* 10/2005 Bavarian et al. ............. 48/198.7

\* cited by examiner

*Primary Examiner* — Jafar Parsa
(74) *Attorney, Agent, or Firm* — Henry E. Naylor

(57) ABSTRACT

A Fischer-Tropsch process for converting a syngas to hydrocarbon products in the presence of a permeable composite fibrous catalytic sheet comprised of at least three distinct solid phases. A first solid phase is a 3-dimensional porous network of a non-conductive porous ceramic material. A second solid phase is an electrically conductive phase comprised of randomly oriented electrically conductive fibers. A third phase is comprised of catalytic particles dispersed on said 3-dimensional porous network, said conductive fibers, or both. A fourth phase can be present, which fourth phase is comprised one or more conductive species or one or more non-conductive species embedded in said first solid phase.

14 Claims, 9 Drawing Sheets

FISCHER-TROPSCH PROCESS USING FIBROUS COMPOSITE CATALYTIC STRUCTURES HAVING AT LEAST THREE SOLID PHASES

CROSS-REFERENCE TO RELATED APPLICATIONS

This is a continuation-in-part of U.S. Ser. No. 11/893,829 filed Aug. 17, 2007.

FIELD OF THE INVENTION

The present invention relates to a Fischer-Tropsch process for converting a syngas to hydrocarbon products in the presence of a permeable composite fibrous catalytic sheet comprised having at least three distinct solid phases. A first solid phase is a 3-dimensional porous network of a non-conductive porous ceramic material. A second solid phase is an electrically conductive phase comprised of randomly oriented electrically conductive fibers. A third phase is comprised of catalytic particles dispersed on said 3-dimensional porous network, said conductive fibers, or both. A fourth phase can be present, which fourth solid phase is comprised one or more conductive species, or one or more non-conductive species, embedded in said first solid phase.

BACKGROUND OF THE INVENTION

Hydrogen is used in the manufacture of many products including edible fats and oils, metals, semiconductors and microelectronics. Hydrogen is also an important fuel source for various energy conversion devices. For example, many types of fuel cells use purified hydrogen and an oxidant to produce electrical energy.

Various processes and equipment are used to produce hydrogen that is consumed by fuel cells. One such piece of equipment is a steam reformer, which reacts water and a hydrocarbonaceous material, such as an alcohol feed in the presence of a steam reforming catalyst to produce a reformate comprised predominantly of hydrogen.

Although catalysts in powder form can be used in chemical process units, catalyst particles are typically formed into shapes such as spheres, pellets and rods. While these shapes are easier to handle, the result in usually a decrease in catalyst activity and/or selectivity.

With diminishing liquid fossil fuel reserves, and the world dependent on such fuels for energy with existing fuel consumption equipment design, infrastructure, and logistics designed for such liquid fuels, it has become increasingly desirable to convert vast reserves of natural gas to liquid fuels. Natural gas is comprised mainly of methane, but it is underutilized due to transportation costs and economic reasons. For example, approximately 50% of the known natural gas deposits in the world (worth trillions of dollars) are in abandoned fields. These fields have significant natural gas deposits, but are located in remote areas, and the amount of reserves does not justify the costs of constructing a transmission pipeline.

Another source of underutilized natural gas is at oil wells, where natural gas is a component of the recovered hydrocarbons. In subterranean oil reserves, the top layer is gas, and though the oil well is constructed to tap into the liquid oil, much of the gas comes to the surface as what is termed associated gas. Typically, the associated gas is flared, except in instances where the oilfield is close to a major gas pipeline.

Gas to liquids (GTL) using the well-known Fischer-Tropsch (FT) reaction has received a great deal of attention in the last few decades. The Fischer-Tropsch process involves a series of chemical reactions that result in the production of a variety of hydrocarbon molecules. The FT process is also one of the most high profile ways to produce synthetic liquid fuel. It converts a mixture of carbon monoxide and hydrogen (syngas) into liquid hydrocarbons of various carbon lengths, such as waxes, paraffins, synthetic diesel and jet fuel.

One of the major issues with the FT process is the rapid increase in temperature after the reaction is initiated. Such a condition needs to be controlled by cooling the reactor at the same rate. This problem has been addressed by many unique reactor designs, but typically requires complicated auxiliary equipment, some of which are redundant for safety reasons.

Another shortcoming of conventional FT processes is the fact that the reaction, by nature, produces about 12 to 34 moles of water for every mole of long chain hydrocarbon, depending on the chain length. This water of reaction is absorbed by the catalyst substrate, which may be at a temperature lower than the boiling temperature of water under the typically high operating pressure of the reactor. This water contributes to deactivation of the catalyst, resulting in frequent catalyst changes/reactivation procedures. The largest component of any GTL plant is the turnover frequency of the catalyst bed. Catalysis experts attribute this drawback to many factors, one of which is the long contact time between reactant gases and catalyst. Thus, it is desirable to use a catalyst system having the ability of better control of local temperatures.

The typical capital cost of a GTL plant, coupled with high operating cost, makes smaller mobile plants uneconomical. Thus, conventional GTL technology cannot be applied to the vast majority of sources of natural gas mentioned above. The plants can usually only be built where an abundant supply of natural gas is guaranteed for a large plant and for a long period of time, such that the billions of dollars that are required to build the plant, can be justified. For example, a recent plant in Qatar, where natural gas is the major hydrocarbon that can be recovered, a GTL plant was built at a cost of 18 to 21 Billion dollars.

While various catalytic reforming processes exist for producing hydrogen from hydrocarbonaceous feeds, such as alcohol feeds, and various Fischer-Tropsch processes exist for producing liquid synthetic fuels from syngas, there remains a need in the art for improvements in process technology, particularly with respect to catalyst utilization, decrease in catalyst turnover rate, and reaction selectivity.

SUMMARY OF THE INVENTION

A method of performing Fischer-Tropsch synthesis, comprising reacting a synthesis gas comprising hydrogen, carbon monoxide, and carbon dioxide by passing it through a permeable composite catalytic sheet-like structure comprised of at least three distinct solid phases wherein: i) a first solid phase is comprised of a 3-dimensional substantially continuous network of a non-conductive porous ceramic material; ii) a second solid phase is comprised of a plurality of electrically conductive fibers integrated throughout the 3-dimensional substantially continuous network of non-conductive porous ceramic material; iii) a third solid phase comprised of an effective amount of Fischer-Tropsch catalyst particles dispersed throughout the non-conductive porous ceramic material, the plurality of electrically conductive fibers, or both, at Fischer-Tropsch reaction conditions.

In a preferred embodiment the Fischer-Tropsch catalyst contains one or more of the catalytic metals Fe, Ni, Co, Ru and Re.

In another preferred embodiment the Fischer-Tropsch process conditions include temperatures from about 150° C. to about 370° C., pressures from about 10 psia to about 600 psia, and catalyst Gas Hourly Space Velocity (GHSV) of about 100 to 50,000/h.

In a preferred embodiment there is a fourth solid phase, which is comprised of a conductive material selected from the group consisting of graphene, graphite, carbon nanostructures such as nanotubes, nanofibers, and nanoribbons.

In another preferred embodiment there is a fourth solid phase which is electrically non-conductive and is comprised of a material selected from the group consisting of ceramic fibers, ceramic nanofibers, and silicon carbide fibers.

In another preferred embodiment, the electrically conductive fibers are selected from the group consisting of carbon fibers, graphitic fibers, and polymer fibers enhanced with grapheme, graphite, carbon and graphitic nanotube, carbon and graphitic nanofibers.

In another preferred embodiment, the carbon fibers are graphitic fibers and the ceramic material is selected from the group consisting of alumina, silica, silica-alumina, titania, zirconia and magnesia.

In another preferred embodiment, the catalyst particles are selected from the group consisting of methanol and natural gas reforming catalysts and Fischer-Tropsch catalysts.

In another preferred embodiment, the catalyst is a Fischer-Tropsch catalyst containing one or more of the elements selected from the group consisting of Co, Zr, Cr, Cu, B, K, and Fe.

In still another preferred embodiment of the present invention there is also present an effective amount of non-conductive ceramic fibers selected from the group consisting of alumina fibers, aluminosilica fibers, aluminoborosilicate fibers, and silicon carbide fibers.

In another preferred embodiment the permeable composite catalytic sheet-like structure is in a form selected from the group consisting of sheet, board, and block.

Also in accordance with the present invention there are provided processes for producing the catalytic sheets-like material of the present invention.

Figure 1:
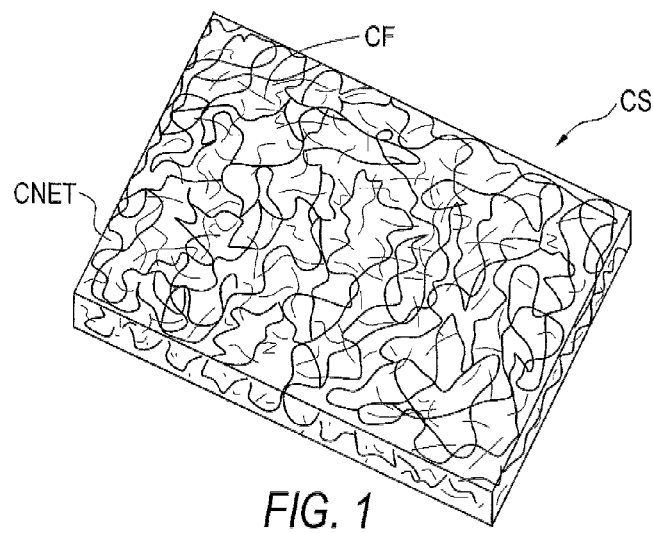
FIG. 1 hereof is a perspective view of a representation of a catalytic sheet of the present invention.

Example 8 hereof is a plot of percent methanol conversion versus methanol flow rate for the data obtained by Example 2 and Examples B-D.

Example 9 hereof is a plot of percent methanol conversion versus methanol flow rate for the data obtained by Examples E-H.

Example 10 hereof is a plot of percent methanol conversion versus methanol flow rate for the data obtained by Examples I-L.

Example 11 hereof is a plot of percent methanol conversion versus methanol flow rate for the data obtained by Examples M-P.

DETAILED DESCRIPTION OF THE INVENTION

The present invention primarily relates to permeable catalytic sheets for use in chemical reactors. Reactants are passed through the sheet, which are brought to reaction temperature by use of an electric current. It is within the scope of this invention that additional heat from an external source can be used, if needed, to reach reaction temperature. The reactants come into contact with catalyst particles contained in, or on the catalytic sheet, thereby initiating the intended chemical reaction and producing the desired product stream. The chemical reaction is enhanced by an electric field created by an electric current passing through the conductive fibers of the permeable catalytic sheet. The permeable catalytic sheets of the present invention are comprised of at least three, preferably at least four, distinct solid phases. The first solid phase is a substantially electrically non-conductive phase characterized as being a 3-dimensional porous network, or matrix, of at least one ceramic material. By "3-dimensional" it is meant that this first solid phase can be thought of as a substantially continuous porous phase as opposed to the second solid phase which is comprised of a plurality of randomly oriented individual electrically conductive fibers, which can be thought of as two dimensional. Any suitable ceramic material can be used. Non-limiting examples of suitable ceramic materials include alumina, silica, silica-alumina, titania, magnesia and the like. Preferred are alumina, silica, and silica-alumina, with alumina being more preferred.

A second solid phase is an electrically conductive phase that is comprised of a plurality of randomly oriented electrically conductive fibers interspersed throughout at least a portion, preferably the entire of the non-conductive first solid phase. Non-limiting examples of conductive fibers suitable for use herein include conductive carbon fibers, graphitic fibers, non-conductive fibers, (preferably polymer fibers) which have been enhanced with an effective amount of conductive carbon species, such as graphene, and carbon and graphitic nanostructures, including nanofibers, nanotubes, and nanoribbons. The term "enhanced" refers to the process of addition of the above mentioned conductive carbon species to non-conductive polymer fibers to give or increase their conductivity. Such addition, or enhancement to the polymer is preferably done before the polymer is spun into a fiber and later carbonized to produce carbon nanofibers. The addition may be made either during the polymerization stage of the polymer or during the molten state before being spun into a fiber.

Any suitable polymer fiber can be treated, or enhanced, with the conductive carbon material. Non-liming examples of such suitable fibers include polyamide fibers, polyester fibers, phenol-formaldehyde fibers, polyvinyl alcohol fibers, polyvinyl chloride fibers, polyolefin fibers, and polyacrylonitrile (PAN) fibers. Preferred are graphitic fibers and carbon fibers based on polyacrylonitrile fibers. One of the leading processes for producing high performance carbon fibers is the so-called PAN process wherein polyacrylonitrile (PAN) is used as a precursor fiber. The PAN process typically starts with a highly prestretched PAN fiber and consists of three steps. The first step is a stabilization treatment wherein the PAN fiber is heat treated in air at a temperature from about 200° to 300° C. for one or more hours. In the second step, the fiber is carbonized at a temperature above about 1100° C. in a non-oxidizing atmosphere. The third step is comprised of a post heat treatment at temperatures up to about 2500° C. to graphitize the fiber and give it its high performance properties. It is in this post heat treatment step that the chemical composition, the crystalline structure, and the mechanical properties, are strongly influenced.

In a preferred embodiment, carbon fibers are heat treated prior to use, such that they develop characteristics of being at least partially graphitic. This is redundant with the third step of the PAN to fiber process. In another embodiment, the starting material, typically a polymeric fiber such as polyacrylonitrile, is impregnated with graphene, graphitic nanofibers of various types, graphite, or carbon nanotubes, to render the fiber electrically conductive before carbonization into the fibers used in this invention. In yet another embodiment, ceramic fibers that have been impregnated with carbon nanostructures of various types, such as carbon nanotubes, carbon nanofibers, carbon nanoribbons, graphene or graphite may be used to impart partial conductivity to the substrate. It has been discovered that such techniques provide a substantially stable and predictable conductivity for the substrate such that automation and precise temperature operation can be achieved.

A third solid phase is comprised of an effective amount of catalyst particles capable of catalyzing the intended chemical reaction. The catalyst particles can be present in bulk form (not on a carrier or support) or on a suitable carrier, such as a metal oxide, preferably alumina. Non-limiting examples of chemical reactions for which the catalytic sheets of this invention can be used include oxidation of volatile organics and perfluorocarbons from semiconductor manufacturing, groundwater remediation, NOx abatement from burners, water-gas shift reactions, Fischer-Tropsch reactions, polymer production, hydrocracking reactions, hydrogen gas production from gaseous hydrocarbonaceous materials such as the steam reforming process involving methanol or methane. If the reaction to be performed with the catalytic sheets of the present invention is the methane steam reforming of methane, then preferred catalysts are nickel based catalysts. Typical reaction conditions for methane steam reforming include temperatures from about 700° C. to about 1000° C.

One preferred chemical reaction is the Fischer-Tropsch reaction where liquid hydrocarbons, preferably synthetic diesel and jet fuels are produced from a syngas comprised primarily of carbon monoxide and hydrogen under suitable conditions in the presence of a Fischer-Tropsch catalyst. In general, Fischer-Tropsch catalysts contain a Group VIII transition metal on a metal oxide support. The catalysts may also contain one or more noble metal promoters and/or crystalline molecular sieves. Suitable Fischer-Tropsch catalysts comprise one or more of Fe, Ni, Co, Ru and Re, with cobalt being preferred. A preferred Fischer-Tropsch catalyst comprises effective amounts of cobalt and one or more of Re, Ru, Pt, Fe, Ni, Th, Zr, Hf, Mg and La on a suitable inorganic support material, preferably one that comprises one or more refractory metal oxides. In general, the amount of cobalt present in the catalyst is from about 1 to about 50 weight percent based on the total weight of the catalyst composition. The catalysts can also contain basic oxide promoters such as $ThO_2$, $La_2O_3$, $MgO$, $ZrO_2$, and $TiO_2$, as well as noble metals (Pt, Pd, Ru, Rh, Os, Ir), coinage metals (Cu, Ag, Au), and other transition metals such as Fe, Mn, Ni, and Re. Useful catalysts and their preparation are known and illustrated in U.S. Pat. No. 4,568,663, which is incorporated herein by reference and which is intended to be illustrative but non-limiting relative to catalyst selection. It will be understood that if a supported Fischer-Tropsch catalyst is used it will preferably be applied to the surface of the non-conductive, or first solid phase. If one or more unsupported Fischer-Tropsch catalytic metals are used then it can be applied to the surface of the conductive fiber (second solid phase) by any suitable plating or coating technique. A non-limiting example of such a technique is electroplating which is well known in the art.

Particularly preferred Fisher-Tropsch catalyst include: those having from 1 to 40 wt. % Co; those containing from about 1 to 30 wt. % Zr; those containing from 1 to 30 wt. % Ce; those containing from 1 to 30 wt. % of a combination of Ce an Zr; those containing Cu; those containing B, those containing K and those containing from 30 wt. % to 70 wt. % Fe. Another preferred family of catalyst suitable for use as Fischer-Tropsch catalyst includes molecular sieves, more preferably the silicoaluminophosphate compositions SAPO, SAPO-11, SAPO-34, and SAPO-13.

Fischer-Tropsch reaction conditions include temperatures of about 300 to 700° F. (149 to 371° C.), preferably about 400 to 550° F. (204 to 228° C.); pressures of about 10 to 600 psia, (0.7 to 41 bars), preferably about 30 to 300 psia, (2 to 21 bars); and gas hourly space velocity (GHSV) of about 100 to 50,000/h.

Another consequential drawback of conventional Fischer-Tropsch synthesis is catalyst deactivation due to coking (carbon soot formation) on the surface of the catalysts. One of the fundamental functional differences between catalysts used for Fischer-Tropsch synthesis or other higher alcohol synthesis, and the ones used for methanol synthesis is whether or not the adsorbed CO molecule dissociates on the catalyst surface. For Fischer-Tropsch synthesis and higher alcohol synthesis, CO dissociation is a necessary reaction condition. For methanol synthesis, the CO bond remains intact. There are many postulations concerning the mechanisms and conditions for such coking, one of which is the presence of water in the substrate, reducing the acidity (electron motion) between the metal substrate interface. Another reason could be the high local temperature conditions created by the exothermic reaction, thus forming elemental carbon deposits on the metal. Yet another consequence of the high local temperatures could be the sintering of the catalyst, thereby reducing the number of the specific coordinate atoms available for absorption of CO into the catalyst. Use of the catalytic sheet structures of the present invention addresses these concerns by maintaining temperature at a local level, and maintaining a high flow of electrons in the catalyst.

When the first non-conductive solid phase and second conductive solid phase are combined, and the third solid phase (catalyst) is dispersed in either the first phase, second phase or both, the resulting catalytic sheet material will have a composite characteristic value of conductivity and resistivity, the value of which will be somewhere between the values of the individual phases. This composite characteristic value defines the current flow and resistive heat that can be generated during the operation of the composite material of this invention comprised of solid phases 1, 2, 3. Catalytic reactions can be exothermic or endothermic, low temperature or high temperature, and therefore require various amounts of electron flow for achieving catalyst activation and performance as well as various reaction temperatures and thermal energy supply to provide the required thermal energy of the reaction.

Depending on the reaction conditions required for the intended use of the catalytic sheet the fourth phase may be needed. This need will typically result when it is not possible to form the first solid phase having the desired resistivity and subsequent resistive heat generating capacity without an undesirable reduction in porosity of the final catalytic sheet. When the composite material of phases 1, 2 and 3 exhibits higher conductivity than required, and also resulting in not enough heat generation to provide a temperature high enough for the given reaction, a fourth solid phase will be an effective amount of electrically non-conductive, or insulating materials, preferably a ceramic material. This non-conductive fourth solid phase preferably consists of fibers or nanofibers made of insulating type materials. By adding two dimensional fibers or nanofibers, the porosity of the composite phase consisting of phases 1, 2 and 3 is not compromised, and remains substantially unchanged.

It will be understood that a fourth solid phase can therefore be present to either increase or decrease the characteristic conductivity and resistive heat generation value of the composite material formed from solid phases 1, 2 and 3. For example, when an increase in conductivity and decrease in resistive heat generation of the composite material comprised of solid phases 1, 2 and 3 is desired, one or more conductive materials will be used for the fourth solid phase. Non-limiting examples of material that can comprise this fourth solid phase when an increase in conductivity and decrease in resistive heat generation is required, are carbon species selected from the group consisting of graphene, graphite, and carbon nanostructures preferably carbon nanofibers, carbon nanotubes and carbon nanoribbons. It is preferred that all of these carbon nanostructures be graphitic and electrically conductive.

The fourth solid phase is preferably embedded in the structure of the first solid phase, which is the non-conductive 3-dimensional phase. The embedding is preferably done during the formation of this first solid phase from a ceramic sol, such as alumina sol. Once the liquid is driven off from the ceramic sol this fourth solid phase will be embedded in the first solid phase. An effective amount of fourth solid phase is embedded into the first solid phase to provide the desired conductivity and resistive heat generation capacity of the new composite material consisting of phases 1, 2, 3 and 4. The amount of material of the fourth solid phase added to the first non-conductive phase is determined by experiments for the desired chemical reaction. In other words, when there is no fourth solid phase present, the conductivity from the second conductive phase, the resistivity from the first solid non-conductive phase and the dispersion of the third solid phase in the first solid phase, in the second solid phase or both, are well suited to provide the characteristics of electron flow and resistive heating required for some reactions, like the methanol steam reforming reaction, as described earlier, there would be no need for a fourth phase.

Given the variety of reaction conditions for various catalytic reactions practiced by industry today, some reactions may need lower reaction temperatures or are exothermic in nature, and require no resistive heat from the composite material, but they do benefit from the higher acidity (higher electron availability) provided by the present invention, because such electron flow enhances the performance of the dispersed catalyst, the third solid phase. Yet other reactions, such as highly endothermic reactions, may need less electron flow but more resistive heat. Hence, while it is not practical to define each and every reaction condition here, it should be understood that the present invention provides for multiple ways to achieve precise reaction conditions and optimizing aids to allow commercial reactions to approach theoretical conditions for the intended catalytic reaction. For each reaction, experimental data can determine whether the composite material is to include 3 or 4 solid phases, and further if the 4th solid phase is to be conducting or non-conducting.

If graphene is used as the fourth solid phase it can be used in an amount from about 0.3 to 3 wt. %. If the carbon or graphitic nanostructures are used then the amount can range from about 3 to 5 wt. %. If the fourth solid phase is graphite or an insulating material such as a ceramic fiber or a silicon carbide fiber, the amount can range from about 20 to 30 wt. %, It is within the scope of this invention that an effective amount of non-conductive ceramic fibers may also be used in the case where the total conductivity of the product catalytic sheet needs to be reduced to a target conductivity. Any suitable non-conductive ceramic fiber can be used for this purpose. This ceramic fiber phase is distinguished from the 3-dimensional non-conductive ceramic phase. For example, the ceramic fibers of this additional solid phase can be thought of as a plurality of 2-dimesional fibers since they are not jointed to one another in a 3-dimensional network. Non-limiting examples of such ceramic fibers that can be used in the practice of the present invention include alumina fibers, aluminosilicate fibers, aluminoborosilicate fibers and silicon carbide fibers. Preferred are aluminosilicate fibers.

Carbon nanostructures, preferably graphitic nanostructures, can be used as a catalyst carrier or they can be used to enhance the conductivity of the resulting catalytic sheets. Non-limiting examples of preferred carbon nanostructures are those selected from carbon nanotubes, carbon fibrils, and carbon nanofibers. Typically, the nanostructures will be substantially graphitic, and in the case of carbon nanofibers and nanotubes, the most preferred nanostructures, the distance between graphitic platelets will be about 0.335 nm. It is to be understood that the terms "carbon filaments", "carbon whiskers", "carbon nanofibers", and "carbon fibrils", are sometimes used interchangeably by those having ordinary skill in the art.

Carbon nanotubes, other than those that are sometimes also referred to as carbon fibrils and those that are the multifaceted type, will typically be of the fullerene type. Such structures are described in an article by M. S. Dresselhaus et. al. entitled Fullerenes, on pages 2087-2092 in Journal of Materials Research, Vol. 8, No. 8, August 1993, which article is incorporated herein by reference. Fullerenes are $C_n$ cage molecules built from a collection of hexagonal and pentagonal faces. The $C_{60}$ fullerenes are typically referred to as "buckminsterfullerenes" or simply "buckyballs". $C_{60}$-derived tubules can be defined, in simplest terms, by bisecting a $C_{60}$ molecule at the equator and joining the two resulting hemispheres with a cylindrical tube one monolayer thick and with the same diameter as $C_{60}$. Cylindrical carbon nanotubes can also be defined as substantially hollow structures comprised of substantially parallel graphite layers aligned at distances of about 0.335 nm to 0.67 nm from each other. It is to be understood that the graphite platelets of the preferred carbon nanofibers of the present invention may have various orientations. For example, they can be aligned parallel, perpendicular, or at an angle with respect to the longitudinal axis of the nanofiber. Further, the surface area of the carbon nanofibers can be increased by careful activation with a suitable etching agent, such as carbon dioxide, steam, or the use of a selected catalyst, such as an alkali or alkaline-earth metal.

In addition, the preferred carbon nanofibers and multifaceted carbon nanotubes of the present invention will have: (i) a nitrogen surface area from about 40 to 300 m²/g; (ii) an electrical resistivity of 0.4 ohm·cm to 0.1 ohm·cm; (iii) a crystallinity from about 95% to 100%; and (iv) a spacing between adjacent graphite sheets of 0.335 nm to about 1.1 nm, preferably from about 0.335 nm to about 0.67 nm, and more preferably from about 0.335 to about 0.40 nm.

The more preferred carbon nanofibers of this invention are those having graphite platelets that are substantially perpendicular to the longitudinal axis of the nanofiber ("platelet" structure) and those wherein the graphite platelets are aligned substantially parallel to the longitudinal axis ("cylindrical" and "multifaceted" tubular). U.S. Pat. No. 6,537,515 to Catalytic Materials, LLC, which is incorporated herein by reference, teaches a method for producing a substantially crystalline graphite nanofiber comprised of graphite platelets that are aligned substantially perpendicular to the longitudinal axis of the nanofiber.

The most preferred carbon nanofibers having their graphite platelets aligned substantially parallel to the longitudinal axis are the non-cylindrical multifaceted tubular nanofibers, also known as "ribbon type" nanofibers. Such multi-faceted tubular nanofibers can be single or multi-walled, preferably multi-walled. By multi-walled we mean that the structure can be thought of a multi-faceted tube within a multi-faceted tube, etc. The multi-faceted tubular carbon nanostructures of the present invention are distinguished from the so-called "fibrils" or cylindrical carbon nanostructures. The multi-faceted tubular nanofibers of the present invention can also be thought of as having a structure that resembles a multi-faceted pencil or Alan key. That is, a cross section of the multifaceted nanotube would represent a polygon. A single wall of the multifaceted nanotubes of the present invention can also be thought of as being a single sheet folded in such a way to resemble a multifaceted tubular structure—the folds being the corners.

It will be understood that the carbon nanostructures used herein can be a separate ingredient embedded into the first solid phase or they can be grown from and be a part of, the electrically conductive carbon fibers, the 3-dimensional non-conductive network, and/or ceramic fibers. The carbon nanofibers of this invention can provide additional conductivity to the final catalytic fibrous structure and thus lower loadings of conductive fiber can be used for the same total conductivity of the fibrous substrate structure.

Figure 3:
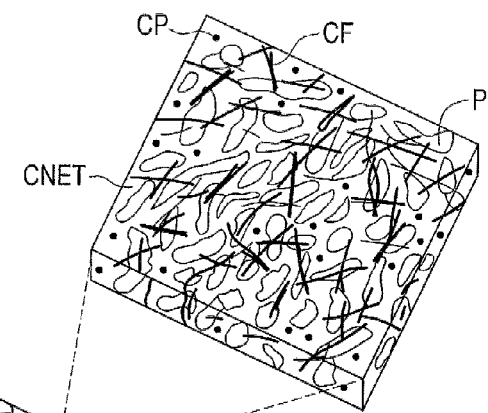
FIG. 3 hereof is an exploded view of a section of the interior of a catalytic sheet of the present invention showing in more detail the relationship of all three phases to each other.
Figure 2:
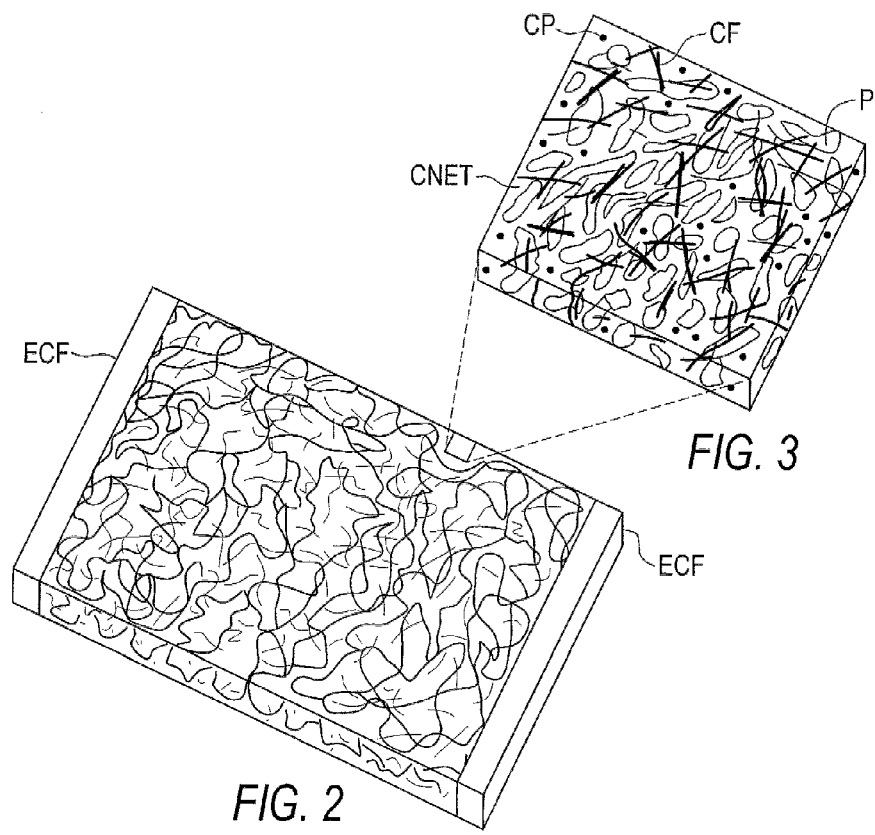
FIG. 2 hereof is a perspective view of the catalytic sheet of FIG. 1 hereof, but containing current feeders on opposing sides.

The present invention can be better understood with reference to the figures hereof. FIG. 1 is an illustration of a perspective view of a preferred catalytic sheet CS of the present invention in the shape of a rectangle having a thickness of about 1 to 30 millimeters. The sheet is comprised of a plurality of randomly oriented conductive fibers CF, a 3-dimensional porous network of electrically non-conductive ceramic material CNET and catalyst particles CP. FIG. 2 shows the catalytic sheet of FIG. 1 hereof except that the sheet now contains electrical current feeders ECF to which an electrical power source can be connected. FIG. 3 hereof is a magnified view of a section of the interior of a catalytic sheet of the invention. FIG. 3 shows the 3-dimensional porous network of ceramic material CNET throughout the sheet and randomly oriented conductive fibers CF. Catalyst particles CP can be seen associated with the 3-dimensional porous network but not the carbon fibers. It will be understood that during the preparation of the catalytic sheet of the present invention small amounts of catalyst particles may become associated with the electrically conductive carbon fibers, but no so much as to adversely affect the intended chemical process.

When electrical power is fed to the current feeder ECF an electrical current is carried through the sheet via the electrically conductive fibers CF. This results in the sheet being heated to reaction temperature because a substantial amount of the carbon fibers are in intimate contact with the 3-dimensional porous network containing the catalyst particles. While the electrically induced heat alone may be enough to catalyze the intended chemical reaction, the plurality of electrically conductive carbon fibers creates an electric field throughout the catalytic sheet, thus providing an unexpected and synergistic effect with regard to the activity of the catalyst. Thus, for a given catalyst activity, or level of reactant conversion, the process can be run at lower temperatures compared to the case when only heat is provided to initiate the chemical reaction and not heat plus an electric field. It will be understood that some chemical reactions may require more heat than is generated by the electric current passing through the conductive carbon fibers. In such cases, additional heat from a conventional source, such as a burner, will be required.

The catalytic sheets of the present invention can be prepared by any suitable method. One preferred method is to prepare the catalytic sheets by a so-call "filtration" method wherein a suspension of catalyst particles is passed an effective amount of time through an electrically conductive fiber mat (one of the solid phases) comprised of a plurality of electrically conductive fibers. The conductive fiber mat will be comprised of a plurality of randomly oriented electrically conductive carbon fibers, preferably graphitic fibers. The total surface area available for contact with reactants of this electrically conductive solid phase will be from about 100 m²/g to about 1500 m²/g, preferably from about 400 m²/g to about 1000 m²/g, and more preferably from about 500 m²/g to about 1000 m²/g. The only limit to the external dimension of the catalyst sheet of the present invention is the process equipment in which it will be used. The bulk density of this electrically conductive solid phase will be an effective bulk density. That is, the bulk density will be enough to provide continuous electrical conductivity from one end of a sheet containing these carbon fibers to an opposing end. It will also allow the reactant feed to pass through it's cross sectional area at sufficient residence time on-catalyst at process flow rates. Further, it will be porous enough so that the pressure drop of a reactant gas (feed) passing through the catalytic sheet will be low enough to carry out the process without extensive pressure drop. Preferred pressure drop should be equal to or less than 5 psig, preferably equal to or less than about 3.0 psig, and more preferably equal to or less than about 1 psig. The porosity of the catalytic sheets will preferably be form about 50 to about 99%, more preferably from about 80 to about 99%. Although this electrically conductive mat can be prepared by molding or pressing a suitable amount of electrically conductive carbon fibers, it is preferred that a pre-manufactured carbon or graphite fiber mat be obtained from a third party, such as Osaka Gas Co., Ltd.

A suspension containing an effective amount of catalyst particles is prepared by use of any suitable liquid dispersing agent. Preferred liquid dispersing agents include water, lower carbon number aliphatic alcohols, as well as any other organic solvents suitable for dispersing the catalyst particles and not cause any significant undesirable effect. More preferred are water, ethanol, and iso-propanol. By "effective amount of catalyst particles" we mean that amount needed in the suspension to result in the desired catalyst loading on the carbon fibers of the mat after a suitable number of times the suspension is passed through the conductive fiber mat. For example, only about 75 wt. % to about 90 wt. % of the catalyst particles in suspension will be transferred to the carbon fibers during any given pass-through, since some of the catalyst particles will always remain with the liquid dispersing agent and not deposit on the carbon fibers. After the predetermined amount of catalyst particles are loaded onto the conductive fiber mat, the catalyst-containing conductive fiber mat is dried to drive off substantially all extraneous dispersing agent. The drying will preferably be done at a temperature from about 85° C. to about 95° C. at atmospheric pressure, although reduced pressures can also be used.

A 3-dimensional non-conductive porous network of ceramic material is formed within the dried catalyst-containing conductive fiber mat. This is preferably done by use of a ceramic sol, more preferably an alumina sol. The alumina sol can be prepared by any suitable means, such as by using boehmite gel powder and 0.5 μm α-alumina particles, such that about 80% of the oxide alumina results from the α-alumina particles and the remaining 20% from the boehmite. If desired, silica sol can be added to the alumina sol to produce a mullite sol. The catalyst-containing conductive fiber mat is soaked in the ceramic sol for an effective amount of time and at about room temperature and atmospheric pressures. That is, for at least that amount of time needed for the sol to infiltrate throughout the conductive fiber mat. During this stage of the procedure a substantial amount, preferably substantially all, of the catalyst particles will migrate from the electrically conductive carbon fibers of the conductive fiber mat to the ceramic sol. The catalytic sheet of the present invention is completed by removing the conductive fiber mat from the sol and drying it under conditions similar to that previously mentioned. The dried catalytic sheet is then calcined in an oxygen-containing atmosphere, preferably air, and at a temperature of about 100° C. to about 500° C., preferably at a temperature of about 250° C. to about 450° C. for an effective amount of time which will typically be from about 0.5 hours to about 24 hours. The dried catalytic sheet is then activated by heating it in a reducing environment, typically in the presence of a hydrogen-containing gas, at a temperature from about 150° C. to about 500° C.

If an effective amount of non-conductive material, such as ceramic fiber is to be used to reduce the total conductivity of the final catalytic sheet, it can be added to the ceramic sol during the preparation of the ceramic sol. An effective amount of carbon nanostructures can also be added during the preparation of the ceramic sol.

Current feeders can now be added to the final catalytic sheet. In a most preferred embodiment, the catalytic sheet is rectangular and one current feed is attached to one side of the sheet and another current feeder to the opposing side. The current feeder can be composed of any suitable conductive metal. It can be attached to the sides of the sheet by merely clamping it onto the sheet. It can also be attached by use of a solder or conductive paste, or by dipping opposing sides of the sheet into a molten conductive metal, then removed and allowed to harden. The current feeder must be physically secure enough to withstand the reaction conditions of the reactor in which the catalytic sheet is to be used. It is within the scope of this invention that the current feeder be part of a holder into which the catalytic sheet is placed for insertion and placement into a catalytic reactor.

In a preferred embodiment of the present invention, the catalytic sheets are prepared by blending together effective amounts of electrically conductive carbon or graphitic fibers and catalyst particles. An effective amount of dispersing liquid is added and the resulting slurry is agitated, preferably by mechanical mixing, until a substantial homogeneous blend results. The blend is then passed through a filter of suitable composition and porosity to obtain a substantially uniform and substantially dry blend of ingredients. The blend in then placed in a vessel of suitable size to which a ceramic sol, as previously described, is added. The blend, plus ceramic sol, is placed in a mold of suitable size and predetermined shape and thickness and dried, as also previously described, to produce a shaped pre-catalytic sheet or mat of predetermined thickness. The pre-catalytic sheet is then calcined as previously described and reduced under reducing conditions and in the presence of a hydrogen-containing gas to produce the catalytic sheet.

Figure 4:
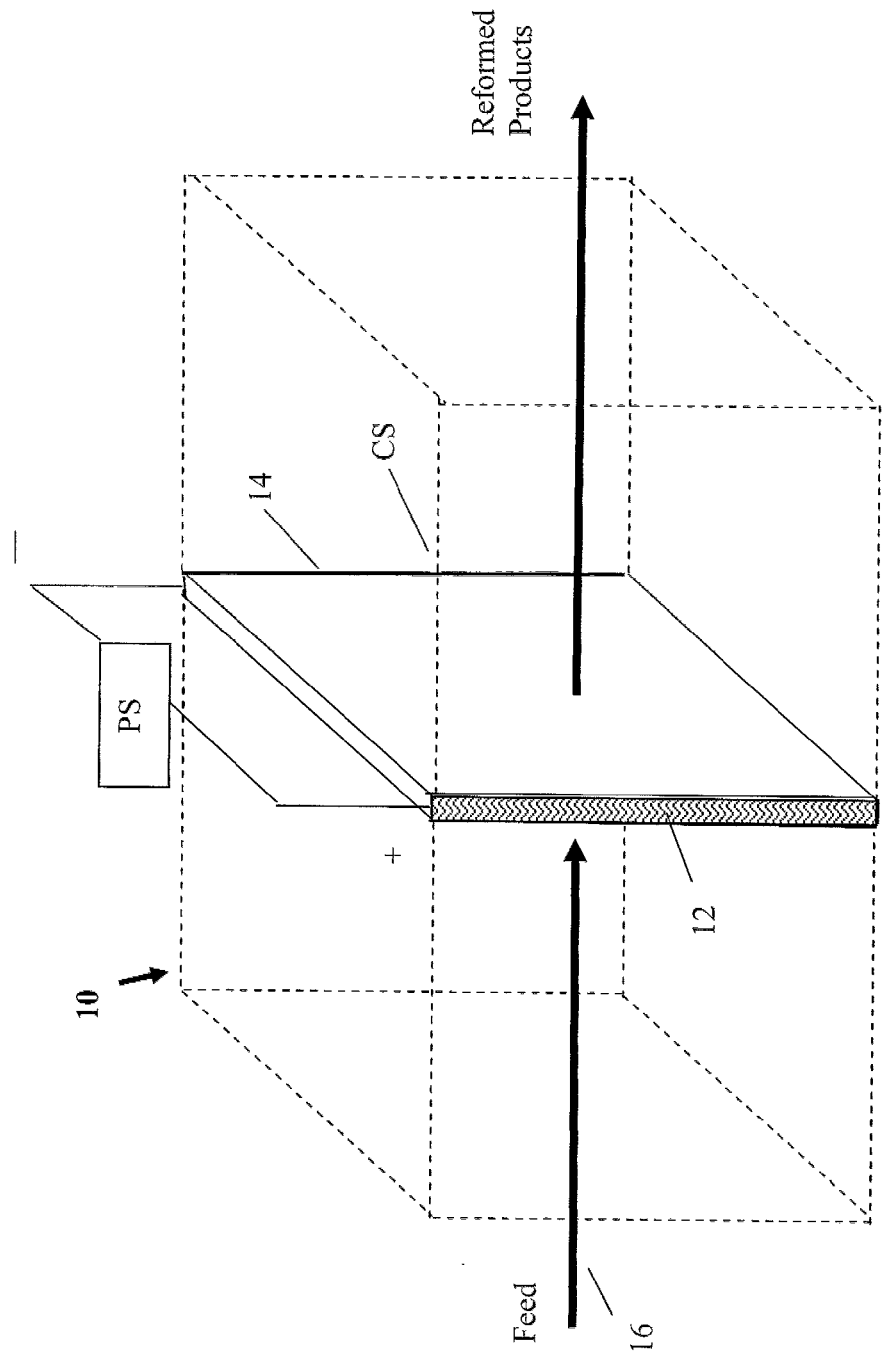
FIG. 4 is a representation of catalyst structure which is subjected to an electrical current and through which a hydrocarbonaceous feedstream, preferably a low carbon number alcohol feedstream is passed.

FIG. 4 hereof is a simplified schematic of a catalytic sheet of the present invention used in a methanol reformer. Catalytic sheet CS is shown in methanol steam reformer reactor 10. The catalytic sheet is connected to an electric power source (PS) by current feeders 12 and 14. The amount of electrical power supplied will be an effective amount. That is, that amount needed to provide and maintain the reaction temperature plus to provide an electrical field throughout the sheet. In the case of the methanol reforming reaction mentioned above, a stream comprised of methanol and steam is introduced via line 16 into the inlet of the methanol reactor and passes through the catalytic sheet CS and reacts with the catalyst particles to produce a hydrogen-rich gas product. The inventor hereof believes that the electric field created by an electric current passing through the conductive fibers of the sheet results in a synergistic effect in combination with the heat of reaction which also provided by the electric current passing through the catalytic sheet. This results in a more active catalyst at any given temperature within the temperature range of the intended reaction. More active catalysts enable the intended process to be conducted at lower bulk reaction temperatures without sacrificing yield or selectivity.

Figure 5:
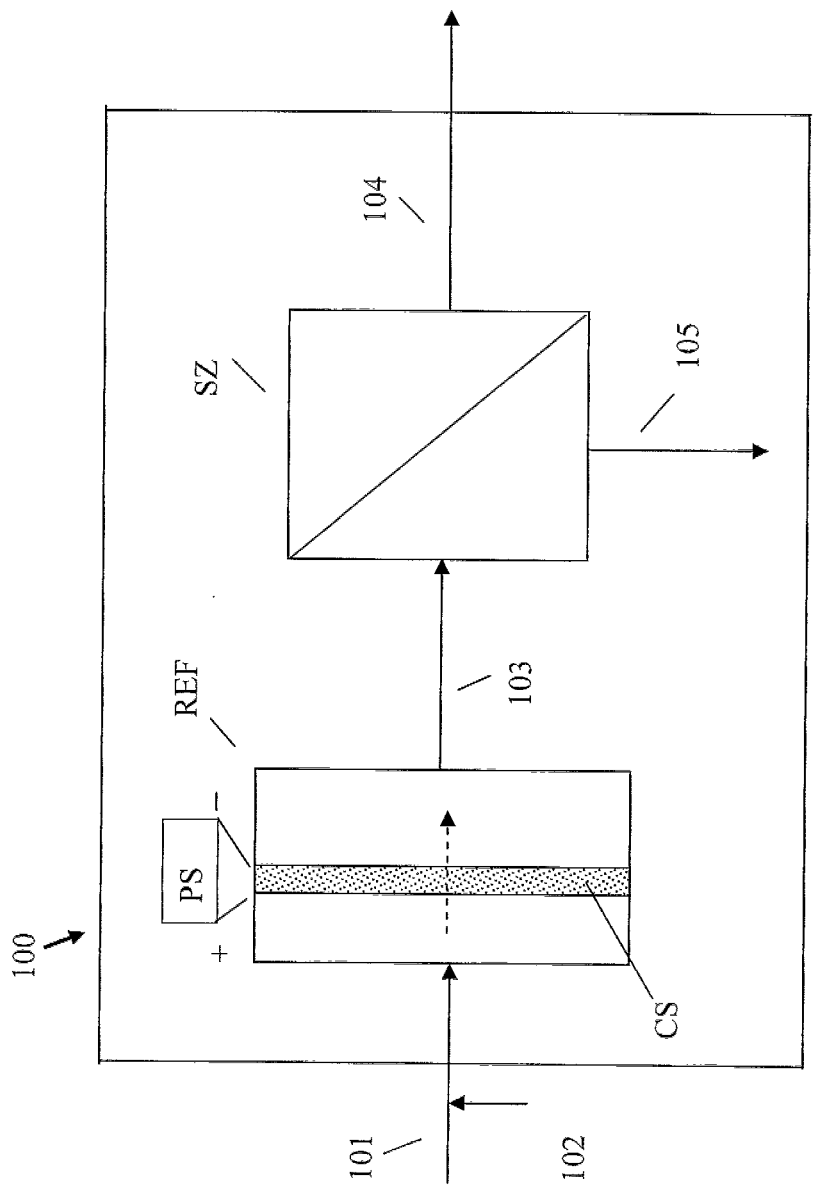
FIG. 5 hereof is representation of a methanol steam reforming process for producing a reformate gas that is passed to a separation zone to increase its' hydrogen concentration.

FIG. 5 hereof is a simplified schematic exemplifying a typical vapor phase reaction by the present invention. The schematic, in this case is of a fuel processing system that contains a fuel processor for producing a product gas stream comprised predominantly of hydrogen. A preferred fuel processor is a steam reformer, which produces the product hydrogen-containing stream by steam reforming a feed stream containing water and a hydrocarbonaceous material. FIG. 5 shows a steam reforming process system generally indicated at 100 and comprised of a steam reformer REF and a gas separation zone SZ. A suitable feed, preferably methanol, is introduced into steam reformer REF via line 101 along with steam via line 102 where it passes through catalytic sheet CS. For example, if the intended reaction is methanol steam reforming (MSR), then it is preferred that the catalyst be a Cu/ZnO on alumina catalyst. Although this figure only shows one catalytic sheet it is to be understood that multiple catalytic sheets can be used in series either layered together or with a gap, or void, between one or more sheets. It is preferred that 2 catalytic sheets of the present invention be used in series with an effective void, or gap between each sheet. A suitable gap between sheets will be about ¼ to about 2 times the thickness of the catalytic sheets. Power supply PS supplies current to the catalytic sheet while feed is passing there through. Steam reformer REF is maintained at suitable temperatures, for example between about 200° C. and 800° C. and at pressures from about 0 psig to about 1000 psig. In some embodiments, feedstream 101 can be delivered to the steam reformer at an elevated temperature, and accordingly can provide at least a portion of the required heat needed for the intended reaction. When a burner or other combustion chamber is used to supply heat, a fuel stream is consumed and a heated exhaust stream is produced. Further, the feedstream is preferably vaporized prior to passing through the catalytic sheet and undergoing the reforming reaction.

While methanol is the feed of choice for producing hydrogen for purposes of this invention other hydrocarbonaceous feedstreams can also be used. Methanol steam reforming (MSR) typically takes place at a lower temperature compared to reforming other hydrocarbonaceous feedstrems. For example, methanol steam reformers typically have reforming regions that are heated to approximately 300° C. to about 500° C., preferably from about 350° C. to about 425° C. Methanol steam reformers also typically receive a feedstream having approximately a 1:1.25 molar ratio of methanol to water (or approximately 64% methanol by weight). This feed ratio may be varied without departing from the scope of the present invention and still produce sufficient amounts of hydrogen gas. Non-limiting examples of other hydrocarbonaceous feedstreams suitable for being treated in accordance with the present invention include the $C_1$ to $C_{11}$ alkanes, $C_1$ to $C_{20}$ alkanols, and petroleum streams such as diesel, kerosene, and naphthas. Petroleum streams may require hydrotreating to remove undesirable heteroatoms, such as sulfur and nitrogen. Preferred hydrocarbonaceous streams are the $C_1$ to $C_3$ alkanes, preferably methane or natural gas. When a naphtha is the hydrocarbon feed, the stream reformer is an on-board reactor for transportation vehicles that produces high purity hydrogen for an on-board fuel cell. Non-limiting examples of suitable $C_1$ to $C_{20}$ alkanols include the $C_1$ to $C_3$ aliphatic alcohols, as well as polyols, such as ethylene glycol and propylene glycol.

Traditionally, low temperature shift catalysts (LTS) have been used as methanol steam reforming catalysts. These catalysts were designed to catalytically facilitate the conversion of water and carbon monoxide to hydrogen and carbon dioxide at temperatures less than about 275° C., such as in the range of about 200 to about 275° C. These catalysts typically are copper-based, such as stabilized compositions of copper and zinc. More particularly, LTS catalysts typically include copper oxide and zinc oxide supported on alumina. LTS catalysts are available in various shapes and forms, such as pellets, powders, etc. LTS catalysts containing copper and zinc will generally include about 10 to 90% copper (I) and/or copper (II) oxide and about 10 to 90% zinc oxide. As used herein, "copper oxide" shall mean copper (I) and/or copper (II) oxide. The LTS catalysts may further include other materials, such as about 0 to 50% alumina. Other examples of LTS catalysts may be described as containing about 20 to 60% copper oxide, about 20 to 50% copper oxide, or about 20 to 40% copper oxide. Still others include these illustrative ranges of copper oxide and about 20 to 60% zinc oxide, about 20 to 50% zinc oxide or about 30 to 60% zinc oxide. Other LTS catalysts contain chromium instead of the copper-zinc formulations described above. An example of a conventional LTS catalyst is made by ICI Chemicals & Polymers, Ltd. of Billingham, England and sold under the trade name 52-1. This LTS catalyst contains about 30% copper (II) oxide, about 45 wt. % zinc oxide and about 13 wt. % alumina. Another example of a LTS catalyst is K3-110, which is made and sold by BASF Corporation. Other examples include G66B and T-2617, which are made and sold by Sud-Chemie, Inc., of Louisville, Ky. Unless otherwise specified herein, all composition percentages are expressed in wt %.

Catalysts used in the practice of the present invention are typically those containing Cu or a Group VIII metal, such as Ni, Rh, Pd or Pt. These metals are preferably supported on a metal oxide support such as alumina, silica, silica-alumina, zirconia or magnesia. Another type of preferred methanol steam reforming catalyst that can be used in the practice of the present invention contains zinc oxide as an active component and does not contain copper oxide as an active component. By "active," it is meant that the component takes part in, or otherwise promotes, the methanol steam reforming reaction and the component is present in at least 3 wt % and often at least 5 or 10 wt % of the active components in the composition. Preferably, but not necessarily in all embodiments, the MSR catalyst contains zinc oxide and chromium oxide as active components. In such a catalyst, the chromium oxide enhances the activity of the zinc oxide. These MSR catalysts may contain at least about 20 wt. % zinc oxide, preferably about 25 wt. % to about 80 wt. % zinc oxide. For example, the catalyst may contain about 30 wt. % to about 70 wt. % zinc oxide, preferably from abut 40 wt. % to about 60 wt. % zinc oxide, more preferably about 50 wt. % zinc oxide. Similarly, the MSR catalyst may contain at least about 20 wt. % chromium oxide, preferably about 25 wt. % to about 80 wt. % chromium oxide. For example, the catalysts may contain about 30 wt. % to about 70 wt. % chromium oxide, preferably from about 40 wt. % to about 60 wt. % chromium oxide, more preferably about 50% chromium oxide.

Other examples of a composition that may be used as a MSR catalyst according to the present disclosure and which exhibits both of the above-discussed properties is sold under the trade name KMA by Sud Chemie. KMA is designed to be used as a high temperature methanol synthesis catalyst. By "high temperature" it is meant a temperature greater than about 700° C. and typically in the range of about 700° to about 900° C. For example, in contrast to an LTS catalyst, KMA has very little activity in the conventional temperature ranges in which LTS catalysts are used, such as 200° C. to about 275° C.

Another example of a suitable MSR catalyst suitable for use herein is a catalyst that contains zinc oxide supported on calcium aluminate. Similar to KMA, this MSR catalyst is not pyrophoric and is not reduced and deactivated by sintering during use. For example, the catalyst may contain up to approximately 95% zinc oxide and at least approximately 3% calcium aluminate. Other illustrative examples of possible compositions include about 25 to about 80 wt. % zinc oxide, about 50 to about 90 wt. % zinc oxide, and about 70 to about 95 wt. % zinc oxide. Similarly, the MSR catalyst may contain at least about 5 wt. % calcium aluminate, about 10 to about 30 wt. % calcium aluminate, about 25 to abut 75 wt. % calcium aluminate or about 40 to about 60 wt. % calcium aluminate. An example of such a catalyst is sold under the trade name G72-E from Sud Chemie. G72-E is designed to be used as a sulfur absorbent material but has proven effective as a MSR catalyst.

Although the above-described MSR catalysts are usually substantially free of copper oxide, it is within the scope of this invention that copper oxide may be present in small quantities, such as less than about 5 wt. % and preferably less than about 1 wt. %. Other examples of MSR catalysts that may offer some performance benefits over the copper-zinc LTS catalysts discussed above (especially when operated at a temperature at or above 300° C.) include high temperature shift catalysts that contain iron oxide. Again, these catalysts are designed for high temperature and/or pressure operation to produce methanol. However, and as discussed herein, the present disclosure is directed to using these catalysts at a moderate (300° to about 500° C.) temperature to produce hydrogen from methanol via steam reforming. Iron oxide is somewhat pyrophoric, but much less so than the copper-zinc LTS catalysts discussed above. Therefore, compared to copper-zinc LTS catalysts, these catalysts offer greater safety and reduced risk of fire when exposed to air. Similar to copper-zinc LTS catalysts, however, these iron oxide-based catalysts may be reduced and deactivated through sintering during use.

A further property that may be exhibited by MSR catalysts according to the present disclosure, either alone or in combination with one or more of the above properties, is that the MSR catalyst minimizes the amount of methane produced during the methanol steam reforming process. It is preferred that substantially no methane be produced during methanol steam reforming. For example, many high temperature shift catalysts and methanol synthesis catalysts, such as iron-based catalysts, produce approximately 1 wt. % to about 5 wt. % methane during a methanol steam reforming reaction. This production of methane, while not detrimental to many applications for the product hydrogen-containing reformate gas stream, and which may be removed or reduced in concentration in a subsequent separation and/or purification step, still reduces the overall yield of hydrogen gas because some of the methanol is reacted to form methane instead of hydrogen gas. KMA and other zinc oxide MSR catalysts meeting the criteria described herein and which do not contain iron oxide as an active component do not tend to produce methane when used as a MSR catalyst in the operating conditions described herein for steam reformer REF.

Hydrogen will be the major, or primary, component of the resulting product gas stream 103. Although product gas stream 103 contains a substantial amount of hydrogen gas, preferably less than or equal to 75 vol. %, the stream may also be referred to as a mixed gas stream because it also contains gases other than hydrogen. Examples of such other gases include carbon dioxide, carbon monoxide, water, methane and/or unreacted methanol as well as other carbon-containing feedstock.

However, many applications require a hydrogen stream that has greater purity and/or a reduced concentration of one or more non-hydrogen components that is present in product gas stream 103. Therefore, steam reformer REF may have an optional separation zone SZ in which the hydrogen purity of the product gas stream is increased and/or the concentration of at least one non-hydrogen component is reduced. As shown in FIG. 5 hereof, separation zone SZ receives the product gas stream 103 and produces a hydrogen-rich stream 104 therefrom. Hydrogen-rich stream 104 will have a greater concentration (or purity) of hydrogen gas than product gas stream 103 and/or has a reduced concentration of at least one non-hydrogen component of the product gas stream.

Separation zone SZ can utilize any suitable separation technology and/or utilize any suitable mechanism, including a pressure-driven mechanism or separation process, to increase the purity of product gas stream 103 and/or remove selected components therefrom, such as to separate product gas stream 103 into hydrogen-rich stream 104 and by-product stream 105. Although only a single one of each of these streams has been schematically illustrated, it is within the scope of the present disclosure that separation zone SZ may produce more than one of each of these streams, which may thereafter be combined before or after leaving the separation region. Similarly, although schematically illustrated as streams in FIG. 5 hereof, it is within the scope of the present invention that the by-product stream be formed from a portion of product gas stream 103 that is split from the stream and stored or otherwise retained within the separation zone and thereafter removed, such as during servicing, replacement of the containment structure, etc. It is also within the scope of the present disclosure that steam reformer REF utilize more than one separation zone and/or utilize more than one type of technology and/or structure for increasing the concentration of hydrogen gas and/or reducing the concentration of selected non-hydrogen components relative to product gas stream 103.

An example of a suitable separation structure for separation zone SZ is one or more hydrogen-permeable and/or hydrogen-selective membranes. The membranes can be formed of any hydrogen-permeable material suitable for use in the operating environment and parameters in which separation zone SZ is operated. Non-limiting examples of suitable materials for membranes include palladium and palladium alloys, and especially thin films of such metals and metal alloys. Palladium alloys have proven particularly effective, especially palladium with 35 wt % to 45 wt % copper. A palladium-copper alloy that contains approximately 40 wt % copper has proven particularly effective, although other relative concentrations and components may be used within the scope of the disclosure.

Hydrogen-selective membranes are typically formed from a thin foil that is approximately 0.001 inches thick. It is within the scope of the present disclosure, however, that the membranes be formed from other hydrogen-permeable and/or hydrogen-selective materials, including metals and metal alloys other than those discussed above as well as non-metallic materials and compositions, and that the membranes may have thicknesses that are greater or less than discussed above. For example, the membrane may be made thinner, with commensurate increase in hydrogen flux. Examples of suitable mechanisms for reducing the thickness of the membranes include rolling, sputtering and etching. A suitable etching process is disclosed in U.S. Pat. No. 6,152,995, the complete disclosure of which is hereby incorporated by reference for all purposes. Non-limiting examples of various membranes, membrane configurations, and methods for preparing the same are disclosed in U.S. Pat. Nos. 6,562,111 and 6,537,352, 6,319,306, and 6,221,117, the complete disclosures of which are hereby incorporated by reference for all purposes.

Another example of a suitable gas separation process that can be used in separation zone SZ is swing absorption. Non-limiting examples of swing adsorption processes that can be used in the practice of the present invention includes conventional pressure swing adsorption, rapid cycle pressure swing adsorption, partial pressure swing adsorption, thermal swing adsorption, and rapid cycle thermal swing adsorption. Accordingly, separation zone SZ can include one or more swing adsorption systems. Pressure swing adsorption (PSA) processes are well known to those having ordinary skill in the art and in such systems gaseous impurities are removed from a stream containing hydrogen gas. PSA is based on the principle that certain gases, under the proper conditions of temperature and pressure, will be adsorbed onto an adsorbent material more strongly than other gases. Typically, it is the impurities that are adsorbed and thus removed from product gas stream 103. The success of using PSA for hydrogen purification is due to the relatively strong adsorption of common impurity gases (such as CO, $CO_2$, hydrocarbons including $CH_4$, and $N_2$) on the adsorbent material. Hydrogen adsorbs only very weakly and so hydrogen passes through the adsorbent bed while the impurities are retained on the adsorbent material. Impurity gases such as $NH_3$, $H_2S$, and $H_2O$ adsorb very strongly on the adsorbent material and are therefore removed from product gas stream 103 along with other impurities. If the adsorbent material is to be regenerated and these impurities are present in product gas stream 103, separation zone SZ preferably includes a suitable device (not shown) that is adapted to remove these impurities prior to delivery of product gas stream to the adsorbent material because it is more difficult to desorb these impurities.

Yet another example of a suitable process for separation zone SZ is a chemical process, in which one or more non-hydrogen components of the product gas stream are chemically reacted to form additional hydrogen gas and/or to form components that are more desirable than the components that are removed from the product gas stream. Illustrative examples of chemical separation processes include the use of at least one methanation catalyst bed to produce methane from carbon monoxide and suitable structure for performing the water-gas shift reaction to produce hydrogen gas from water and carbon monoxide present in the product gas stream.

For example, in the context of a steam reformer that is producing a fuel stream for a fuel cell stack containing a plurality of fuel cells, many fuel cells are subject to damage if exposed to certain components, such as carbon monoxide and/or carbon dioxide above certain threshold concentrations. For at least many conventional proton-exchange membrane (PEM) fuel cells, the concentration of carbon monoxide should be less than 10 ppm (parts per million). Preferably, the system limits the concentration of carbon monoxide to less than about 5 ppm, and even more preferably, to less than about 1 ppm. The concentration of carbon dioxide may be greater than that of carbon monoxide. For example, concentrations of less than about 25 wt. % carbon dioxide may be acceptable. Preferably, the concentration is less than about 10 wt. %, and even more preferably, less than about 1 wt. %. Especially preferred concentrations are less than about 50 ppm. The acceptable maximum concentrations presented herein are illustrative examples, and concentrations other than those presented herein may be used and are within the scope of the present disclosure. For example, particular users or manufacturers may require minimum or maximum concentration levels or ranges that are different than those identified herein. Similarly, when steam reformers according to the present disclosure are used with a fuel cell stack that is more tolerant of these impurities, then the product hydrogen stream may contain larger amounts of these gases. Similarly, when the steam reformers are used to produce product hydrogen streams that are used for applications other than as a fuel stream for a fuel cell stack, it may be desirable to remove other components from the product hydrogen stream and/or it may not be necessary to utilize a separation process.

As previously mentioned, steam reformer process system 100 can utilize more than one type of separation process and/or include or be associated with more than one type of separation structure. For example, when the hydrogen-rich product stream is intended for use in a PEM fuel cell stack or other device that will be damaged if the stream contains more than determined concentrations of carbon monoxide or carbon dioxide, it may be desirable to include a methanation catalyst in one of the separation zones. The methanation catalyst converts carbon monoxide and carbon dioxide into methane and water, both of which will not damage a PEM fuel cell stack. A polishing zone (not shown) may also be used downstream of the one or more separation zones SZ and may also include a steam reforming catalyst to convert any unreacted feedstock into hydrogen. Thus, it is optional to include a downstream, or secondary, reforming zone. In such an embodiment, it is preferable that the reforming catalyst is upstream from the methanation catalyst so as not to reintroduce carbon dioxide or carbon monoxide downstream of the methanation catalyst.

Figure 6:
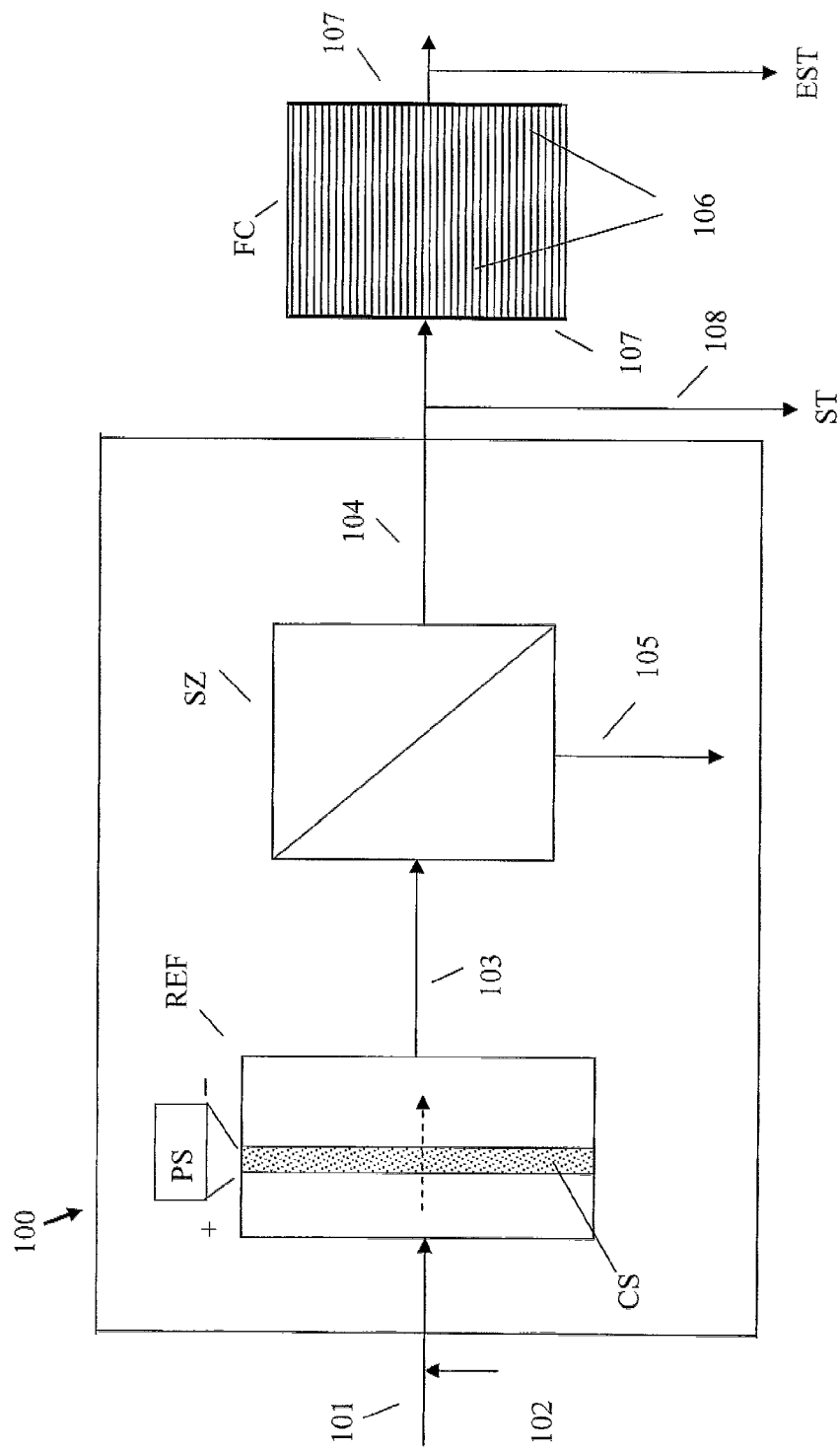
FIG. 6 hereof is a representation of a steam reforming process for producing a reformate gas that is treated to increase its hydrogen purity, which purified hydrogen stream is fed to a fuel cell.

As schematically illustrated in FIG. 6 hereof, steam reformer REF according to the present disclosure can be adapted to deliver at least a portion of a high purity hydrogen stream 104 to at least one fuel cell stack FC. Fuel cell stack FC receives the portion of the product hydrogen stream and an oxidant and produces an electric current therefrom. Non-limiting examples of suitable oxidants include air, oxygen gas, and oxygen-enriched air. The oxidant stream may be delivered to the fuel cell stack via any suitable mechanism. Although the steam reforming process system is indicated at 100 in FIG. 6, it is within the scope of the present invention that any of the steam reformers previously disclosed herein may be incorporated with a fuel cell system. Fuel cell stack FC is adapted to produce an electric current from that portion of product hydrogen stream 104 delivered thereto. In the illustrated embodiment, a single steam reformer system 100 and a single fuel cell stack FC are shown and described. However, more than one of either, or both of these components, may be used. It is also within the scope of the present invention that these components have been schematically illustrated and that the fuel cell system may include additional components that are not specifically illustrated in FIG. 6, such as feed pumps, air delivery systems, heat exchangers, controllers, flow-regulating structures, sensor assemblies, heating assemblies, power management modules, and the like.

A fuel cell stack typically includes multiple fuel cells 106 joined together between common end plates 107, which contain fluid delivery/removal conduits (not shown). Examples of suitable fuel cells include proton exchange membrane (PEM) fuel cells and alkaline fuel cells. Fuel cell stack FC can receive all of product hydrogen stream 104. Some or all of hydrogen stream 104 may additionally, or alternatively, be delivered, via a suitable conduit, for use in another hydrogen-consuming process, burned for fuel or heat, or stored for later use. For example, and as illustrated in FIG. 6 hereof, it is within the scope of the disclosure that at least a portion of the product hydrogen stream produced by the steam reformer be conducted via line 108 in a suitable hydrogen storage device ST. Non-limiting examples of suitable storage devices for hydrogen gas include pressurized tanks and hydride beds. When the fuel cell system includes a steam reformer and a hydrogen storage device ST, the hydrogen gas that is delivered to fuel cell stack FC may come from reformer REF, storage device ST, or both. A portion of the hydrogen can even come from an external source as well. Fuel processing and fuel cell systems according to the present disclosure may also be constructed without a hydrogen storage device.

The electric current produced by fuel cell stack FC may be used to satisfy the energy demands, or applied load, of at least one associated energy-consuming device (not shown). Non-limiting examples of such energy-consuming devices include motor vehicles, recreational vehicles, industrial or construction vehicles, boat or other seacraft, tools, lights or lighting assemblies, appliances (such as a household or other appliance), households, commercial offices or buildings, neighborhoods, industrial equipment, signaling or communication equipment, the balance-of-plant electrical requirements for the fuel cell system, etc. It is within the scope of the present invention that the fuel cell system may (but is not required to) include at least one energy-storage device EST which is adapted to store at least a portion of the current produced by fuel cell stack FC. Described in other words, the current may establish a potential that may be later used to satisfy an applied load, such as from an energy-consuming device. An illustrative example of a suitable energy-storage devices is a battery, but others may be used, such as ultra capacitors and flywheels. Energy storage device EST may additionally or alternatively be used to power the fuel cell system, such as during startup of the system.

The following examples are presented for illustrative purposes only and are not to be taken as being limiting in any way.

EXAMPLE 1 AND COMPARATIVE EXAMPLE A

Preparation of Catalytic Sheet

The following procedure, which is sometimes referred to herein as the "filtration procedure", was used to prepare a plurality of catalytic sheets for these two examples.

A suspension was prepared by mixing 40 g of a commercial CuO/ZnO catalyst in 1000 ml iso-propanol at room temperature, and treated with ultrasonic at about room temperature (18° C. to 21° C.) for 2 hours. The commercial CuO/ZnO catalyst used was in powder form having a density of 65 to 85 lb/ft and with particles sizes ranging from about 300 μm to about 1 mm and available from Süd-Chemie Inc. with the designation C18-AMT. A 9 cm diameter carbon fiber felt having a thickness of 10 mm and weighing 3.5 g was placed on a Buchner funnel and placed on a filtering flask. The carbon fiber felt mat was pretreated by oxidizing it with $H_2O_2$. The carbon fiber mat acts as a filter. The carbon fiber mat, which is available from Osaka Gas Chemicals Co. Ltd was comprised of electrically conductive carbon fibers having an average fiber diameter of about 10 μm and average unit weight of about 500 g/m. The CuO/Zn catalyst in iso-propanol suspension was poured through the carbon fiber mat until the suspension was substantially depleted of catalyst, thus indicating that substantially all of the catalyst was taken up by the carbon fiber mat. The so treated carbon fiber mat was then dried at a temperature of about 100° C. for about 5 hrs. It was found that about 34 g. of CuO/ZnO catalyst was loaded onto the carbon fiber mat.

The dried mat, which had sponge-like appearance, was then soaked in 100 g of alumina sol designated Al$_2$O from Nyacol Nano Technologies, Inc. which was comprised of 20 wt. % alumina in deionized water. The alumina particle size was about 50 nm. After soaking in the alumina sol the treated carbon fiber mat was dried and calcined at about 350° C. for about 10 hours. The result was a 61 g catalytic sheet characterized as having three distinct solid phases. A first solid phase was comprised of a 3-dimentional network of porous/fibrous alumina (from the sol) that was interspersed throughout the carbon fiber mat, which carbon fiber mat represents a second solid phase. It was observed that substantially all of the catalyst particles (third solid phase) had migrated from the carbon fiber mat to the 3-dimensional alumina network.

Use of Catalytic Sheet in Methanol Reforming

For each run for each example a section of the catalytic sheet measuring 1.25×1.25×0.3 inch$^3$ was cut to fit into the methanol reforming apparatus used in these examples. This section of catalytic sheet had an overall weight of about 7.0 g; contained 3.9 g. of catalyst, 0.55 g. of carbon fibers, 2.55 g of 3-dimensional alumina network and a resistance of 7 ohms. The section of catalytic sheet was positioned in a methanol steam reforming reactor so that a methanol feedstream could pass through the sheet perpendicular to the face of the sheet. The temperature at which the methanol steam reforming was performed for Example 1 was 150° C. and was provided by use of an electric current that was passed through the catalytic sheet at a power (P) about 28 watts. The temperature at which the methanol steam reforming was conducted for Comparative Example A was 250° C. and was provided by use of an oven into which the reformer apparatus was placed. No electric current was passed through the catalytic sheet for Comparative Example A. Each example was performed without the use of an argon reference gas, each was run at various feed rates as shown in Table I below, and each at a steam to carbon ration of about 1.5 and a methanol/steam feed rate from about 0.05 to 0.2 ml/min. The product gas exiting the reactor was trapped by water at about 0° C. and the collected methanol/water mixture was analyzed by GC-FID (Gas Chromatography-Flame Ionization Detector). Table I below shows the results from these two Examples.

TABLE I

| MeOH (sccm) | Example 1 Conversion of MeOH (%) | Comparative Example A Conversion of MeOH (%) | GHSV (/hr) |
| --- | --- | --- | --- |
| 17 | 93 | 80 | 324 |
| 33 | 80 | 71 | 648 |
| 66 | 66 | 50 | 1296 |

Figure 7:
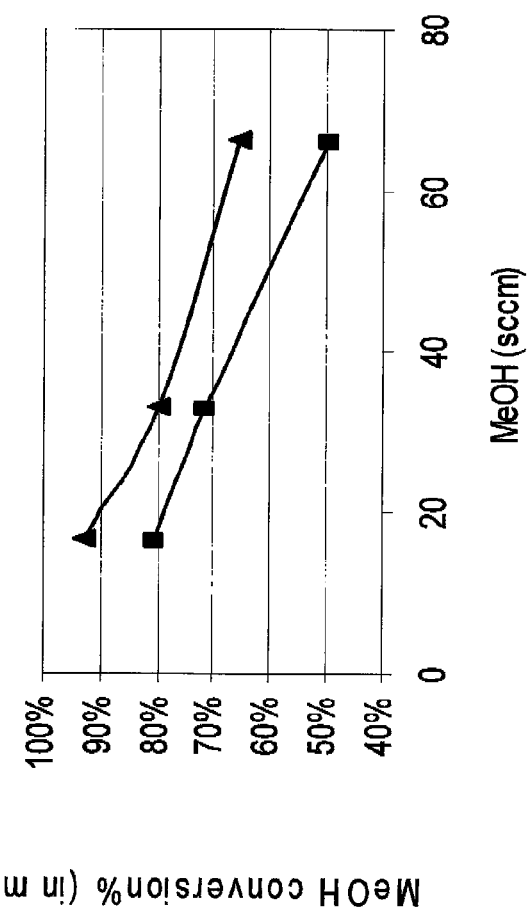
FIG. 7 hereof is a plot of percent methanol conversion versus methanol flow rate in standard cubic centimeters per minute (sccm) for the data obtained by Example 1 and Comparative Example A.

FIG. 7 hereof is a plot of the data of Table I which evidences that greater methanol conversion can be achieved at lower temperatures when the catalytic sheet of the present invention is heated by use of an electric current that is passed through the sheet was opposed to more conventional heating in an oven.

EXAMPLE 2 AND COMPARATIVE EXAMPLES B-D

The following procedure, which is sometimes referred to herein as the "mixing procedure" was used to prepare a plurality of catalytic sheets for these two examples.

20 g of the commercial CuO/ZnO catalyst used for the above examples were mixed with 4 g of chopped electrically conductive carbon fibers and 100 g of the alumina sol as used in above examples. The mixture was introduced into a 2 ft×2 ft×0.7 ft mold. The molded mixture was dried at about 95° C. for 10 hours then calcined at about 350° C. for 5 hours. 1.25×1.25×0.35 inch$^3$ sections of the molded sheet were cut for testing in the methanol steam reforming apparatus of these examples. Each resulting catalytic sheet weighed 6.2 g and contained 3.9 g of catalyst and 2.3 gram of alumina. The electrical resistance of the sheet was 60 ohms. The catalytic sheets also contained three distinct solid phases. A first solid phase was comprised of a 3-dimentional network of porous/fibrous alumina (from the alumina sol), a second solid phase comprised of the carbon fibers interspersed throughout the 3-dimensional alumina network and catalyst particles (third solid phase) substantially all of which were found on the 3-dimensional alumina network and not the on the carbon fibers.

Use of Catalytic Sheet in Methanol Reforming

Methanol steam reforming was performed as in the above examples. The temperature for Example 2 was 150° C. which was provided by an electric current at 28 watt power being applied to the catalytic sheet. The temperatures for Comparative Examples B, C and D were provided by an oven at temperatures 250° C., 200° C. and 150° C. respectively. No electric current was passed through the catalytic sheets for the Comparative Examples B-D. The level of methanol conversion was measured for each and the results are set forth in Table II below.

TABLE II

| MeOH (sccm) | Example 1 Conversion of MeOH (%) | Comparative Example B Conversion of MeOH (%) | Comparative Example C Conversion of MeOH (%) | Comparative Example D Conversion of MeOH (%) | GHSV (/hr) |
| --- | --- | --- | --- | --- | --- |
| 17 | 93 | 87 | 83 | 38 | 324 |
| 33 | 91 | 72 | 61 | 36 | 648 |
| 66 | 82 | 66 | 51 | 31 | 1296 |

Figure 8:
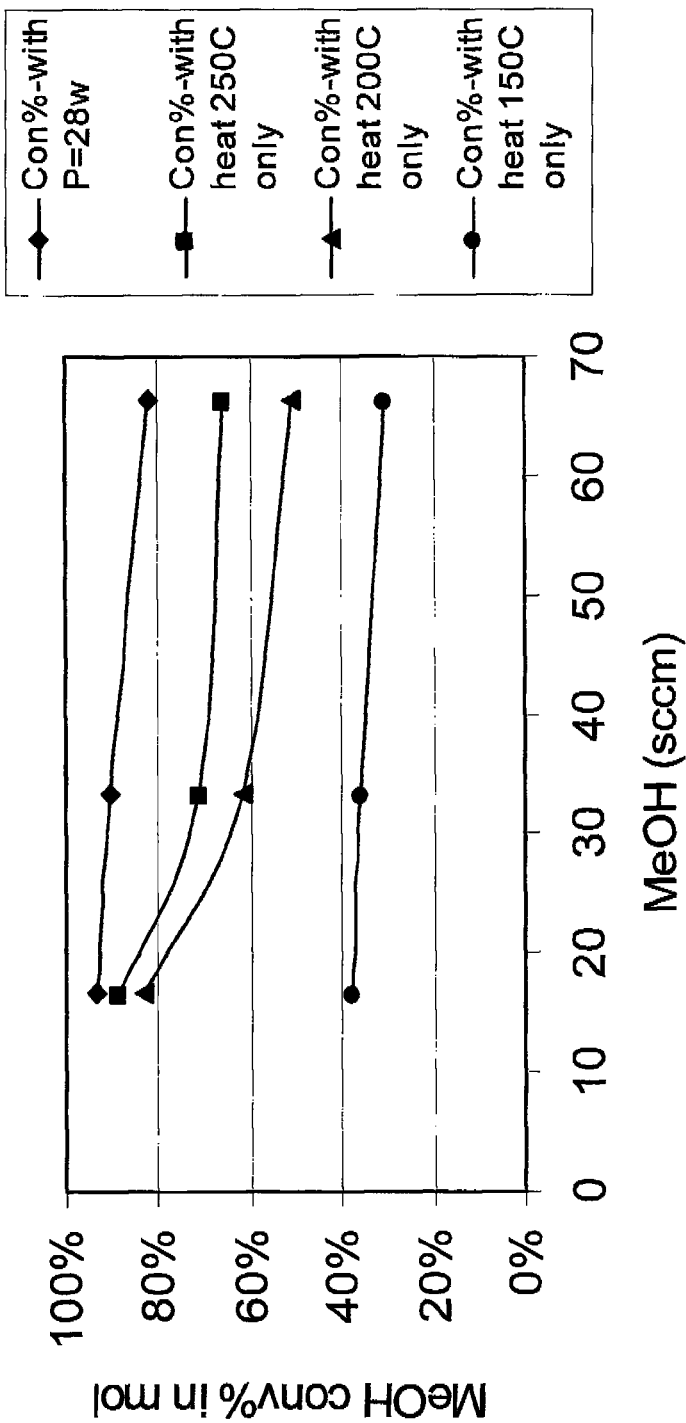

FIG. 8 hereof is a plot of the data of Table II which again evidences that greater methanol conversion can be achieved at lower temperatures when the catalytic sheet of the present invention is heated by use of an electric current that is passed through the sheet was opposed to more conventional heating in an oven.

COMPARATIVE EXAMPLES E-H

The filtration procedure of Example 1 and Comparative Example A was followed for preparing catalytic sheets except no alumina sol was used. Methanol steam reforming reactions were run with the resulting catalytic sheets, which now contained the catalyst particles on the carbon fiber mat instead of on a 3-dimensional non-conductive network. The temperature of Comparative Example E was 150° C. which was provided by an electric current at 28 watt power being applied to the catalytic sheet. The temperature for Comparative Examples F, G and H was provided by an oven at temperatures 250° C., 200° C. and 150° C. respectively. No electric current was passed through the catalytic sheet for Comparative Examples F-H. The level of methanol conversion was measured for each and the results are set forth in Table III below.

TABLE III

| MeOH (sccm) | Comparative Example E Conversion of MeOH (%) | Comparative Example F Conversion of MeOH (%) | Comparative Example G Conversion of MeOH (%) | Comparative Example H Conversion of MeOH (%) | GHSV (/hr) |
| --- | --- | --- | --- | --- | --- |
| 17 | 94 | 89 | 72 | 46 | 324 |
| 33 | 78 | 75 | 57 | 21 | 648 |
| 66 | 56 | 55 | 46 | 19 | 1296 |

Figure 9:
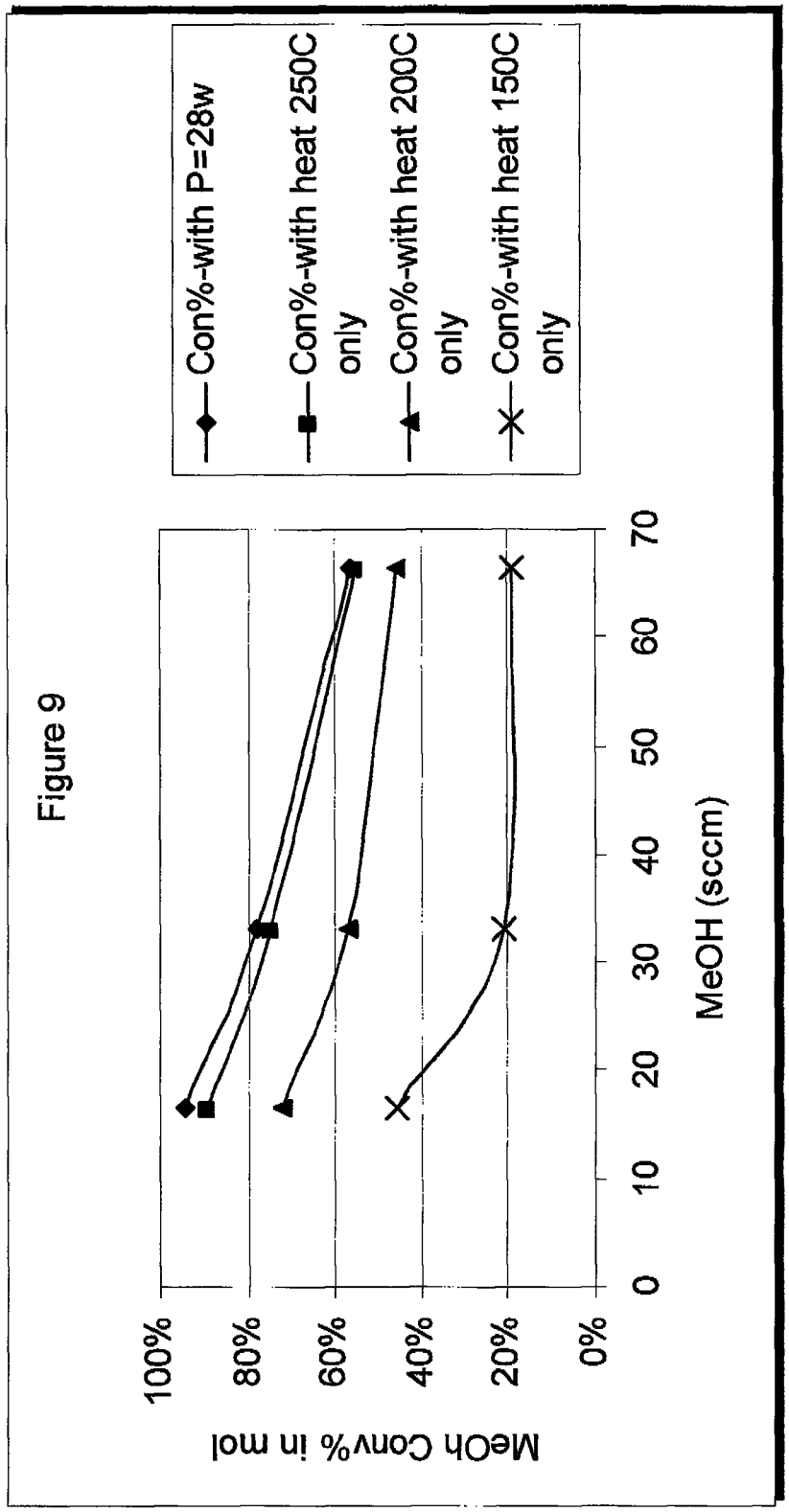

FIG. 9 hereof is a plot of the data of Table III which evidences that greater methanol conversion can be achieved at lower temperatures when the catalytic sheet of the present invention is heated by use of an electric current that is passed through the sheet was opposed to more conventional heating in an oven.

COMPARATIVE EXAMPLES I-L

The following procedure was used to prepare a plurality of catalytic sheets for these four comparative examples.

A $Cu^{2+}/Zn^{2+}$ solution was prepared by mixing 15 g Copper (II) nitrate·2.5 $H_2O$ and 15 g Zinc(II) nitrate·6 $H_2O$ with deionized water/ethanol=30/30 mL. To this solution there was added a 9 cm diameter carbon fiber felt. The carbon fiber felt mat was pretreated by oxidizing it with $H_2O_2$. The thickness of this felt was 10 mm and weighed 3.5 g. The so treated carbon fiber felt was dried at 100° C. for 30 min, then an aqueous solution of $NH_4OH$ (pH=12, prepared by $NH_4OH$ (30%) 20 mL, and 20 mL ethanol) was introduced into the mixture. The metal salts were converted to $Cu(OH)_2$ and $Zn(OH)_2$, and these metal hydroxides were directly loaded onto carbon fiber felt. The metal hydroxide treated carbon felts was then dried at 100° C. for 4 hours. The resulting sheets were then calcined at 350° C. for 3 hours, and reduced with $H_2/Ar$ at 15/100 sccm, and at 250° C. for 2 hours to obtain a structure comprised of Cu/ZnO catalyst on the carbon fiber felt.

9.9 g of a CuO/ZnO commercial catalyst identified for Example 1 was loaded onto the carbon fiber felt. Sample sizes of the catalytic sheets measuring 1.25×1.25×0.3 inch³ weighing 2.0 g were cut for placement in the methanol reforming apparatus of the present invention. These sheet samples contained 1.45 g of catalyst, 0.55 g of carbon fiber, after reduction, and had an electrical resistance of 50 Ohms.

The sample of catalytic sheets were used in methanol steam reforming in accordance with the procedure for the above examples except that the temperature for Comparative Example I was 150° C. which was provided by an electric current at 30 watt power being applied to the catalytic sheet. The temperature for Comparative Examples J, K, and L was provided by an oven at temperatures of 250° C., 200° C. and 150° C. respectively. No electric current was passed through the catalytic sheets for Comparative Examples J-L. The level of methanol conversion was measured for each and the results are set forth in Table IV below.

Figure 10:
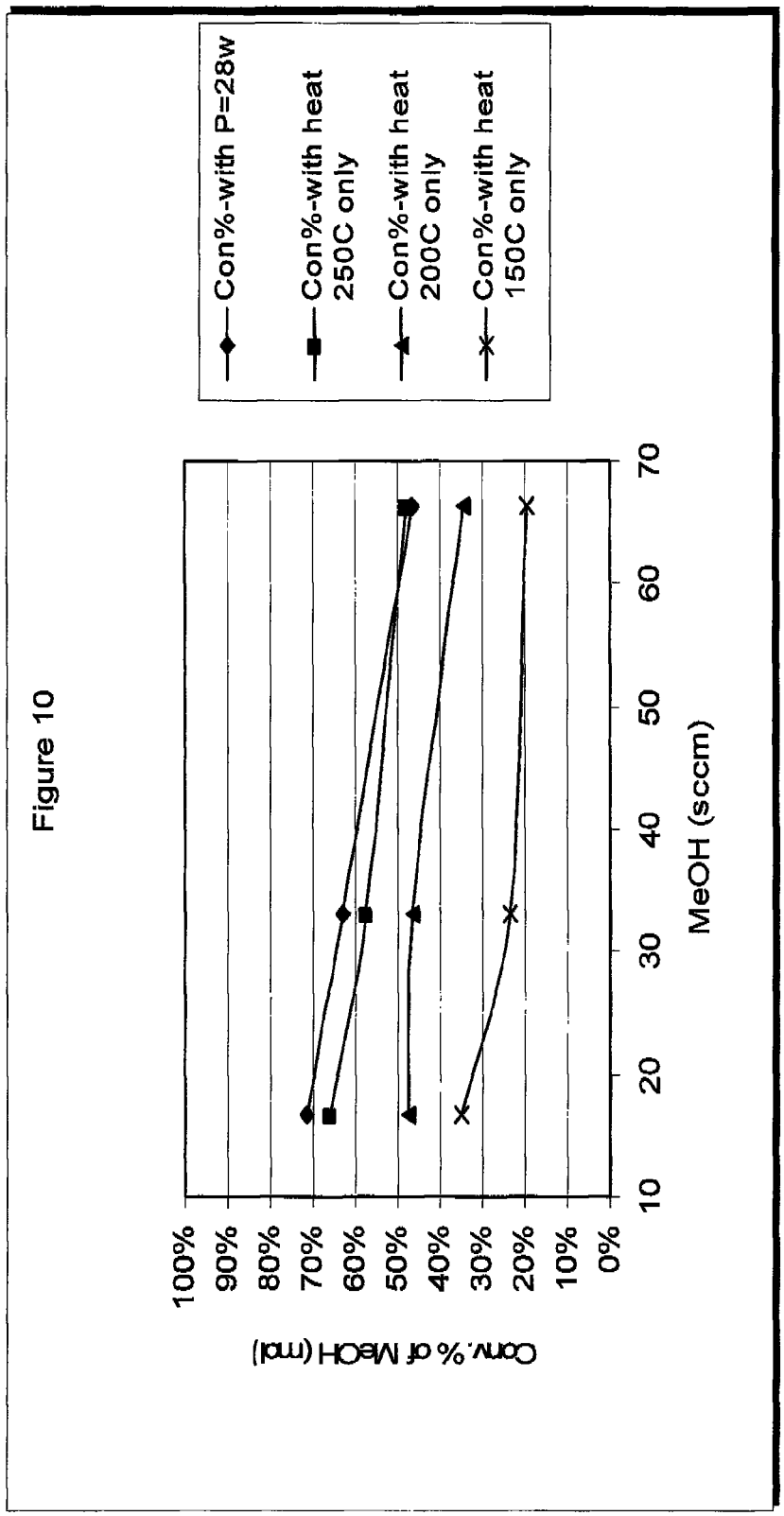

FIG. 10 hereof is a plot of the data of Table IV which evidences that the greatest level of methanol conversion is found when the catalyst particles are located on the non-conductive ceramic (alumina) network and not on the carbon fibers when an electric current is passed through the catalytic sheet.

COMPARATIVE EXAMPLES M-P

The following procedure was used to prepare a plurality of catalytic sheets for these four comparative examples.

A $Cu^{2+}/Zn^{2+}$ solution was prepared by mixing 15 g Copper (II) nitrate·2.5 $H_2O$ and 15 g Zinc(II) nitrate·6 $H_2O$ with deionized water/ethanol=30/30 mL. To this solution there was added a 9 cm diameter carbon fiber felt. The carbon fiber felt mat was pretreated by oxidizing it with $H_2O_2$. The thickness of this felt was 10 mm and weighed 3.5 g. The so treated carbon fiber felt was dried at 100° C. for 30 min, then an aqueous solution of $NH_4OH$ (pH=12, prepared by $NH_4OH$ (30%) 20 mL and 20 mL ethanol) was introduced into to the above mixture. The metal salts were converted to $Cu(OH)_2$ and $Zn(OH)_2$, and these metal hydroxides were directly loaded onto carbon fiber felt. The metal hydroxide treated carbon felts was then dried at 100° C. for 4 hours. The resulting sheets were then calcined at 350° C. for 3 hours, and reduced with $H_2/Ar$=15/100 sccm ratio, at 250° C. for 2 hours to obtained Cu/ZnO-Carbon fiber felt.

10.6 g of a CuO/ZnO commercial catalyst identified for Example 1 was loaded onto the carbon fiber felt. Sample sizes of the catalytic sheets measuring 1.25×1.25×0.3 inch³ weighing 1.9 g were cut for placement in the methanol reforming apparatus of the present invention. These catalytic sheet samples contained 1.45 g of catalyst, 0.55 g of carbon fiber and was immobilized by use of the $AL_2O$ alumina sol, and dried at 90° C. for 3 hours. The weight of substrate was 3.2 g. After reduction the electrical resistance of the catalytic sheet samples was about 60 ohms The sample of catalytic sheets were used in methanol steam reforming in accordance with the procedure for the above examples except that the temperature for Comparative Example M was 150° C. which was provided by an electric current at 28 watt power being applied to the catalytic sheet. The temperatures for Comparative Examples N, O and P were provided by an oven at temperatures 250° C., 200° C. and 150° C. respectively. No electric current was passed through the catalytic sheets for Comparative Examples N-P. The level of methanol conversion was measured for each and the results are set forth in Table V below and FIG. 11 hereof.

TABLE IV

| MeOH (sccm) | Example 1 Conversion of MeOH (%) | Comparative Example I Conversion of MeOH (%) | Comparative Example J Conversion of MeOH (%) | Comparative Example K Conversion of MeOH (%) | Comparative Example L Conversion of MeOH (%) | GHSV (/hr) |
| --- | --- | --- | --- | --- | --- | --- |
| 17 | 93 | 72 | 66 | 48 | 35 | 324 |
| 33 | 80 | 63 | 57 | 46 | 24 | 648 |
| 66 | 66 | 46 | 48 | 35 | 20 | 1296 |

TABLE V

| MeOH (sccm) | Example 1 Conversion of MeOH (%) | Comparative Example M Conversion of MeOH (%) | Comparative Example N Conversion of MeOH (%) | Comparative Example O Conversion of MeOH (%) | Comparative Example P Conversion of MeOH (%) | GHSV (/hr) |
|---|---|---|---|---|---|---|
| 17 | 93 | 78 | 51 | 50 | 45 | 324 |
| 33 | 80 | 73 | 48 | 46 | 44 | 648 |
| 66 | 66 | 48 | 44 | 42 | 43 | 1296 |

Figure 11:
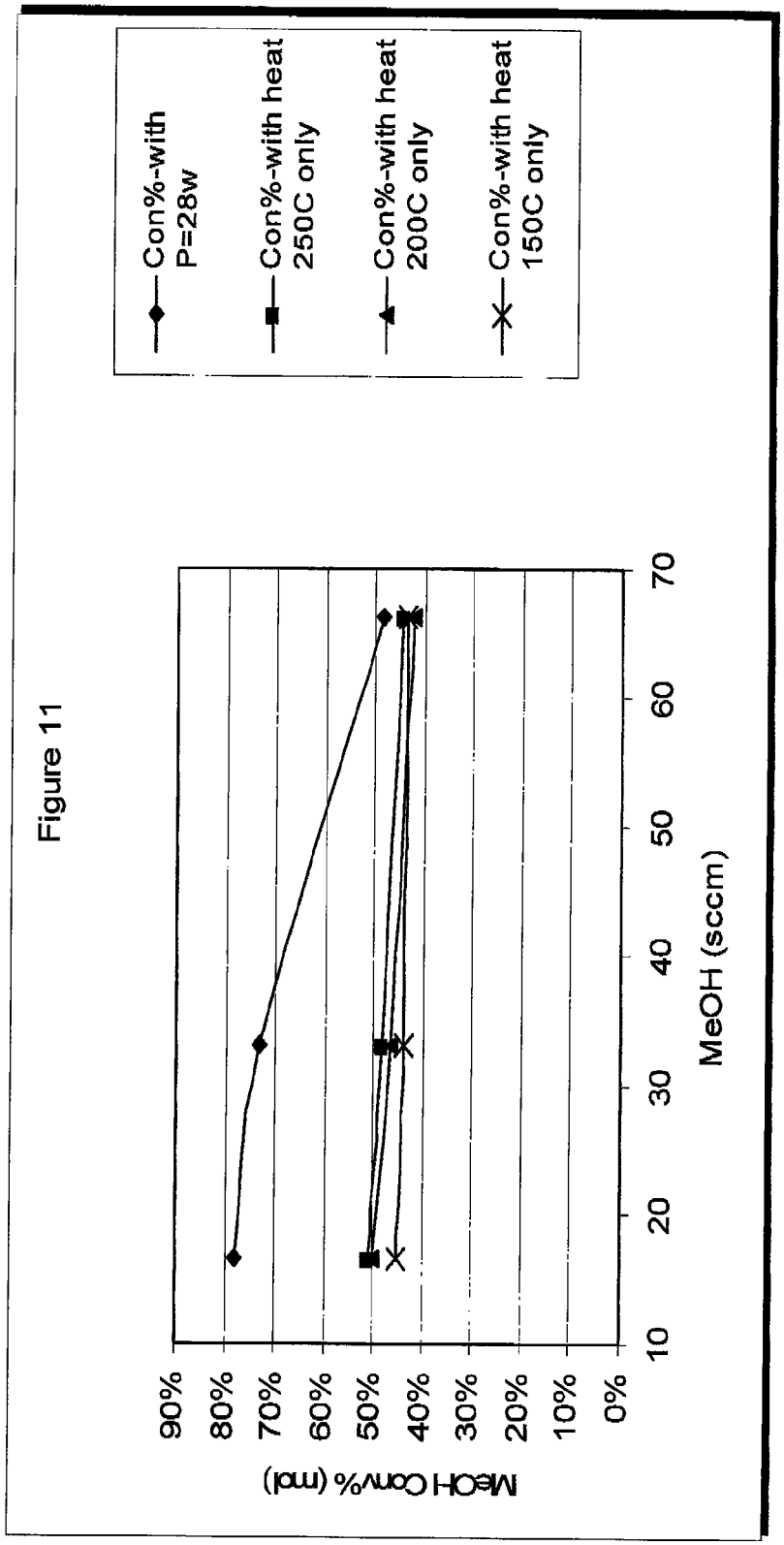

FIG. 11 hereof is a plot of the data of Table V which again evidences that the greatest level of methanol conversion is found when the catalyst particles are located on the non-conductive ceramic (alumina) network and not on the carbon fibers when an electric current is passed through the catalytic sheet.

EXAMPLE 3 AND COMPARATIVE EXAMPLE Q

The following experimental data is presented in a comparison format with published data on catalyst performance during the Fischer-Tropsch reaction for various innovative catalysts. The formulations of the catalyst and experimental conditions in the publications cited in these following examples were duplicated for a direct comparison between conventional methods and the electrically activated methods of catalysis of the present invention.

The focus of this set of examples is on producing higher carbon chain paraffins, which are more valuable than lower chain carbons. Referenced composition and experimental procedure is found in Jong Wook Bae, Seung-Moon Kim, Seon-Ju Park, Sai Prasad, Yun-Jo Lee & Ki-Won Jun; Ind. Eng. Chem. Res., 2009, 48, 3228-3233, which is incorporated herein by reference. This publication teaches an amorphous aluminum phosphate ($AlPO_4$)-supported cobalt catalyst with Ru promotion with a final formulation of 20% Co-0.5% Ru—$AlPO_4$. This catalyst was made by sequential impregnation of $AlPO_4$ with an aqueous solution of cobalt(II) nitrate and $Ru(NO_3)_2(NO_2)_2$, with drying and calcination being performed after addition. n was the highest performing catalyst. This catalyst is identified herein as Catalyst A. Catalyst B, a catalyst of this invention, was prepared by taking the catalyst particles of Catalyst A. For exact weight, the weight composition ratios were taken as the main factor. The amount of catalyst was determined by the space velocity published. With a constant ratio, and running the experiment at the given space velocity.

Preparation of Catalyst B

A suspension was prepared by containing an effective amount of particles of Catalyst A in 1000 ml of iso-propanol. A 9 mm×9 mm×10 mm carbon fiber mat as referenced in Example 1 hereof was immersed in the suspension for 30 minutes. The catalyst-containing carbon fiber mat was dried at 85° C. at about atmospheric pressure. For exact weight, the weight composition ratios were taken as the main factor. The amount of catalyst was determined by the space velocity published, using a constant ratio, and running the experiment at the given space velocity.

An alumina sol was prepared by using boehmite gel powder and 0.5 μm α-alumina particles, such that about 80% of the oxide alumina resulted from the α-alumina particles and the remaining 20% from the boehmite. The catalyst-containing carbon fiber mat was soaked in the alumina sol for 1 hour at room temperature and atmospheric pressure. The graphite fiber mat was removed from the sol and dried at 85° C. at atmospheric pressure. The dried catalytic sheet was then calcined in air, at a temperature of 300° C. for 8 hours. The dried catalytic sheet was then activated by heating it in hydrogen atmosphere, at a temperature of 300° C.

Experimental tests for both catalysts were also carried out as outlined in the referenced paper, with the exception of an electric current on the catalyst substrate of Catalyst B:

$H_2$:CO mole ratio=2:1

SV=2000 L/Kg-cat/h

Product distribution is given in C-Mol %.

Duration 60 hours.

Pressure 2.0 mPa.

TABLE VI

| Temp.(° C.) | CO Conv. (%) | T.O. Freq. × $10^{-2}$ | $C_1$ % | $C_2$-$C_4$ % | $C_5$-$C_7$ % | $C_8$+ % | Exp. Error % | (V) | (A) |
|---|---|---|---|---|---|---|---|---|---|
| Referenced Catalyst RuCo/$AlPO_4$ ||||||||||
| 220° C. | 29.3 | 1.7 | 15.1 | 10.9 | 12.4 | 61.6 | 0% | N/A | N/A |
| 240° C. | 72.3 | 4.2 | 17.3 | 15.1 | 14.2 | 53.4 | 0% | N/A | N/A |
| Fibrous Catalyst Substrate with RuCo/$AlPO_4$ ||||||||||
| 190° C. | 42.1 | No Deactivation | 10.2 | 10.1 | 12.3 | 66.4 | 1% | 37 | 2 |
| 220° C. | 75.4 | No Deactivation | 10.8 | 8.2 | 10.0 | 70.1 | 0.9% | 37.6 | 2.4 |
| 240° C. | 85.0 | No Deactivation | 11.4 | 12.3 | 11.3 | 65.2 | 0.2% | 37.2 | 3.0 |

It clear from the above table that the electrically activated fibrous three dimensional catalyst sheet of the present invention imparts higher selectivity, higher conversion and turnover, while performing equal to or better than the published Catalyst A at lower temperatures. Most importantly, it shows no deactivation during the 60 hour on-stream operation.

EXAMPLE 4 AND COMPARATIVE EXAMPLE R

The focus of this set of experiments is on conversion rates. Catalyst C is a comparative catalyst of Example 2 of U.S. Pat. No. 6,897,177 which is incorporated herein by reference. It's composition if represented by 40-g Co/0.1-g Pt/100-g Al2O3, but is referred to as catalyst E in the 177 patent.

Catalyst D, a catalyst of this invention, was prepared by taking particles of Catalyst C. For exact weight, the weight composition ratios were taken as the main factor. The amount of catalyst was determined by the space velocity published, using a constant ratio, and running the experiment at the given space velocity.

Preparation of Catalyst D:

A suspension was prepared by containing an effective amount of particles of Catalyst C in 1000 ml of iso-propanol. A 9 mm×9 mm×10 mm carbon fiber mat as referenced in Example 1 hereof was immersed in the suspension for 30 minutes. The catalyst-containing carbon fiber mat was dried at 85° C. at atmospheric pressure.

An alumina sol was prepared by using boehmite gel powder and 0.5 μm α-alumina particles, such that about 80% of the oxide alumina resulted from the α-alumina particles and the remaining 20% from the boehmite. The catalyst-containing carbon fiber mat was soaked in the alumina sol for 1 hour at room temperature and atmospheric pressure. The graphite fiber mat was removed from the sol and dried at 85° C. at atmospheric pressure. The dried catalytic sheet was then calcined in air, at a temperature of 300° C. for 8 hours. The dried catalytic sheet was then activated by heating it in hydrogen atmosphere, at a temperature of 300° C.

Experimental tests for both catalysts were also carried out as outlined in the referenced paper, with the exception of an electric current on the catalyst substrate of Catalyst C:

$H_2$=49.1 vol %; CO=25.9 vol %; $CH_4$=9.3 Vol %; $CO_2$=0.5 Vol %; Ar=15.2 Vol %; SV=2169 mL/gcat/h; Duration 15 hours; Pressure 20.3 bar; Amount of catalyst 20.8 grams Temperature=220.5° C.

A conversion rate on a ($H_2$+CO) basis of 76% is reported for Catalyst C.

This experiment using Catalyst D resulted in a ($H_2$+CO) conversion rate of 87% with a 37 V-3.2 amp power across the substrate.

Lower temperature experiment at 190° C. was performed, and conversion rate of 79% was achieved with a 35 V-2 amp power applied across the substrate.

No degradation of the catalyst was observed over the 15 hour run.

It is clear from this example that the electrically activated fibrous three dimensional catalyst sheet of the present invention imparts higher conversion at lower temperatures. Most importantly, it shows no deactivation during the 15 hour on-stream operation.

What is claimed is:

1. A method of performing Fischer-Tropsch synthesis, comprising reacting a synthesis gas comprising hydrogen and carbon monoxide, by passing it through a permeable composite catalytic sheet-like structure comprised of at least three distinct solid phases wherein: i) a first solid phase is comprised of a 3-dimensional substantially continuous network of a non-conductive porous ceramic material; ii) a second solid phase is comprised of a plurality of electrically conductive fibers integrated throughout the 3-dimensional substantially continuous network of non-conductive porous ceramic material; iii) a third solid phase comprised of an effective amount of Fischer-Tropsch catalyst particles dispersed throughout the non-conductive porous ceramic material, the plurality of electrically conductive fibers, or both, at Fischer-Tropsch reaction conditions.

2. The method of claim 1 wherein the Fischer-Tropsch catalyst contains one or more of the catalytic metals Fe, Ni, Co, Ru and Re.

3. The method of claim 1 wherein the Fischer-Tropsch catalyst is comprised of effective amounts of cobalt and one or more of Re, Ru, Pt, Fe, Ni, Th, Zr, Hf, Mg and La.

4. The method of claim 1 wherein the Fischer-Tropsch catalyst contains a silicoaluminophosphate composition selected from the group consisting of SAPO, SAPO-11, SAPO-34, and SAPO-13.

5. The method of claim 1 wherein the Fischer-Tropsch process conditions include temperatures from about 150° C. to about 370° C., pressures from about 10 psia to about 600 psia, and catalyst gas hourly space velocity of about 100 to 50,000/h.

6. The method of claim 1 wherein there is a fourth solid phase comprised of a plurality of one or more conductive or non-conductive materials embedded within said first solid phase.

7. The method of claim 1 wherein the conductive fibers are selected from the group consisting of carbon fibers, graphitic fibers, and polymer fibers enhanced with graphene, graphite, carbon and graphitic nanotube, carbon and graphitic nanofibers.

8. The method of claim 7 wherein the conductive fibers are graphitic fibers.

9. The method of claim 1 wherein the conductive fibers are graphitic fibers.

10. The method of claim 1 wherein the ceramic material of the first solid phase is selected from the group consisting of alumina, silica, silica-alumina, titania, zirconia, and magnesia.

11. The method of claim 10 wherein the ceramic material is alumina.

12. The method of claim 6 wherein the fourth solid phase is comprised of one or more conductive materials selected from the group consisting of graphene, and carbon and graphitic nanostructures, selected from the group consisting of nanofibers, nanotubes, and nanoribbons.

13. The catalytic sheet of claim 6 wherein the fourth solid phase is a non-conductive phase comprised of a non-conductive material selected from the group consisting of ceramic fibers, zirconia fibers, alumina fibers, aluminosilica fibers, aluminoborosilicate fibers, ceramic nanostructures, and silicon carbide fibers.

14. The catalytic sheet of claim 10 wherein the ceramic fibers are selected from the group consisting of ceramic nanostructures and silicon carbide fibers.

* * * * *